(12) United States Patent
Lenker et al.

(10) Patent No.: US 7,722,568 B2
(45) Date of Patent: May 25, 2010

(54) EXPANDABLE INTRA-AORTIC BALLOON PUMP SHEATH

(75) Inventors: Jay A. Lenker, Laguna Beach, CA (US); Joseph Bishop, Menifee, CA (US); George F. Kick, Casa Grande, AZ (US); Edward J. Nance, Corona, CA (US)

(73) Assignee: Onset Medical Corporation, Irvine, CA (US)

( * ) Notice: Subject to any disclaimer, the term of this patent is extended or adjusted under 35 U.S.C. 154(b) by 12 days.

(21) Appl. No.: 12/021,097

(22) Filed: Jan. 28, 2008

(65) Prior Publication Data

US 2008/0183136 A1    Jul. 31, 2008

Related U.S. Application Data

(60) Provisional application No. 60/887,112, filed on Jan. 29, 2007.

(51) Int. Cl.
  *A61M 5/178*  (2006.01)
  *A61M 29/00* (2006.01)
  *A61M 37/00* (2006.01)

(52) U.S. Cl. .............. 604/164.03; 604/96.01; 604/4.01

(58) Field of Classification Search ............ 604/164.03, 604/4.01, 96.01, 101.01–101.05
See application file for complete search history.

(56) References Cited

U.S. PATENT DOCUMENTS

| | | | |
|---|---|---|---|
| 4,338,942 A | 7/1982 | Fogarty | |
| 4,401,433 A | 8/1983 | Luther | |
| 4,738,666 A | 4/1988 | Fuqua | |
| 5,059,183 A | 10/1991 | Semrad | |
| 5,092,839 A | 3/1992 | Kipperman | |
| 5,250,025 A | 10/1993 | Sosnowski et al. | |
| 5,295,994 A | 3/1994 | Bonutti | |
| 5,320,611 A | 6/1994 | Bonutti | |
| 5,395,349 A | 3/1995 | Quiachon et al. | |
| 5,514,091 A | 5/1996 | Yoon | |
| 5,527,336 A | 6/1996 | Rosenbluth | |
| 5,662,614 A | 9/1997 | Edoga | |
| 5,716,373 A * | 2/1998 | Wolvek et al. | 606/194 |
| 5,766,203 A | 6/1998 | Imran et al. | |
| 5,776,141 A | 7/1998 | Klein et al. | |

(Continued)

FOREIGN PATENT DOCUMENTS

EP         0206553         1/1991

(Continued)

*Primary Examiner*—Nicholas D Lucchesi
*Assistant Examiner*—Rebecca E Eisenberg
(74) *Attorney, Agent, or Firm*—Knobbe, Martens, Olson & Bear, LLP.

(57) ABSTRACT

Disclosed is an expandable transluminal sheath, for introduction into the body while in a first, low cross-sectional area configuration, and subsequent expansion of at least a part of the distal end of the sheath to a second, enlarged cross-sectional configuration. The sheath is configured for use in the vascular system and has utility in the introduction and removal of balloon counterpulsation catheters. The access route is through the femoral arteries and the iliac arteries into the aorta, where an intra-aortic balloon pump catheter is positioned to provide cardiac support. The distal end of the sheath is maintained in the first, low cross-sectional configuration during advancement to the arteries into the aorta. The distal end of the sheath is subsequently expanded using a radial dilatation device.

20 Claims, 10 Drawing Sheets

U.S. PATENT DOCUMENTS

| | | | |
|---|---|---|---|
| 6,168,579 B1 | 1/2001 | Tsugita | |
| 6,183,443 B1 | 2/2001 | Kratoska et al. | |
| 6,197,016 B1 | 3/2001 | Fourkas et al. | |
| 6,312,443 B1 | 11/2001 | Stone | |
| 6,358,238 B1 | 3/2002 | Sherry | |
| 6,537,247 B2 | 3/2003 | Shannon | |
| 6,616,678 B2 | 9/2003 | Nishtala et al. | |
| 6,638,268 B2 | 10/2003 | Niazi | |
| 6,706,017 B1 | 3/2004 | Dulguerov | |
| 6,726,651 B1 * | 4/2004 | Robinson et al. | 604/101.01 |
| 2001/0012950 A1 | 8/2001 | Nishtala et al. | |
| 2002/0009535 A1 | 1/2002 | Michal et al. | |
| 2002/0072680 A1 * | 6/2002 | Schock et al. | 600/486 |
| 2002/0077653 A1 | 6/2002 | Hudson et al. | |
| 2002/0099431 A1 | 7/2002 | Armstrong et al. | |
| 2003/0032974 A1 * | 2/2003 | Leschinsky et al. | 606/192 |
| 2004/0006344 A1 | 1/2004 | Nguyen et al. | |
| 2004/0059179 A1 * | 3/2004 | Maguire et al. | 600/16 |
| 2005/0085842 A1 | 4/2005 | Eversull et al. | |
| 2005/0124937 A1 | 6/2005 | Kick et al. | |
| 2005/0149105 A1 | 7/2005 | Leeflang et al. | |
| 2005/0222576 A1 | 10/2005 | Kick et al. | |

FOREIGN PATENT DOCUMENTS

| | | |
|---|---|---|
| WO | WO/99/17665 | 4/1999 |
| WO | WO/03/090834 | 11/2003 |

\* cited by examiner

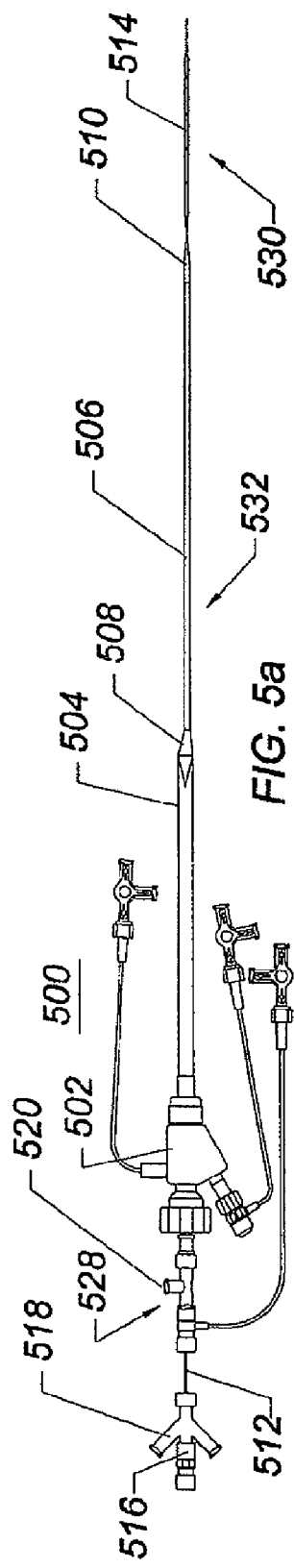
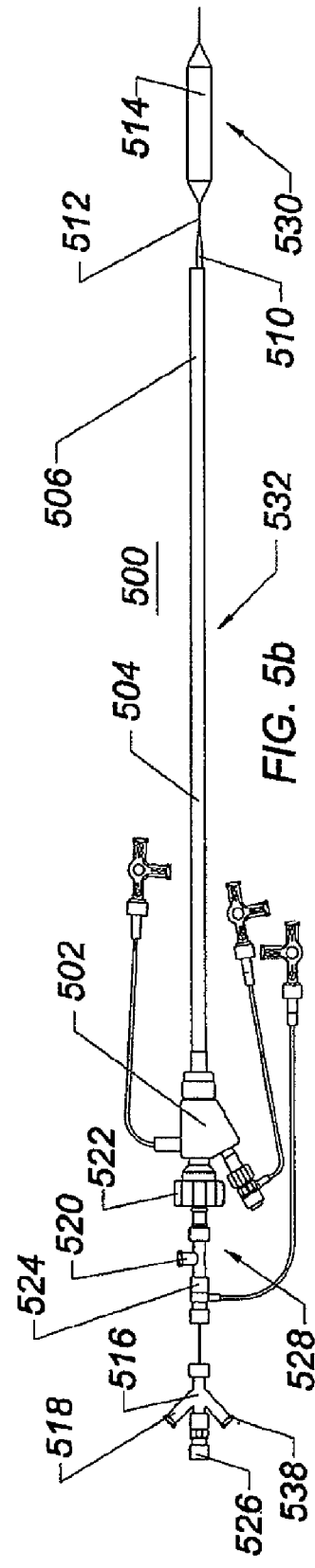
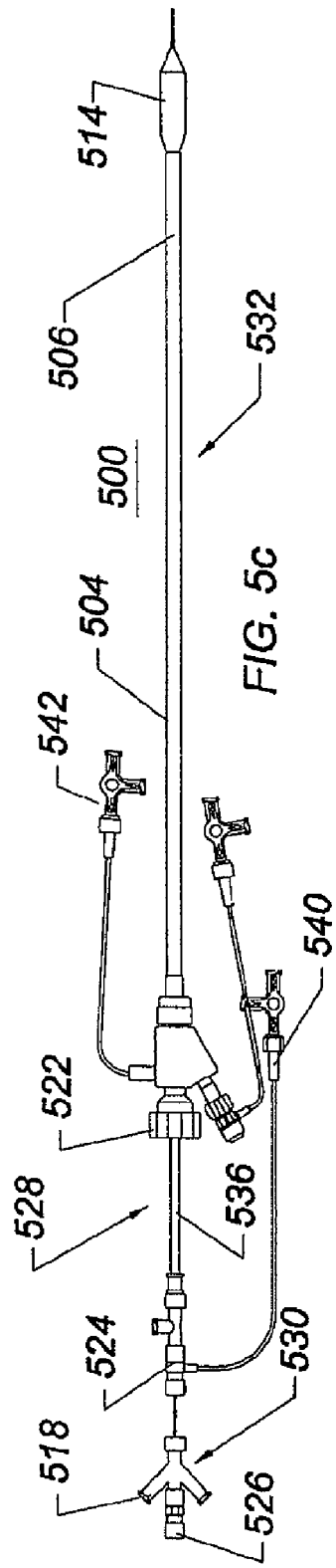
FIG. 5a
FIG. 5b
FIG. 5c

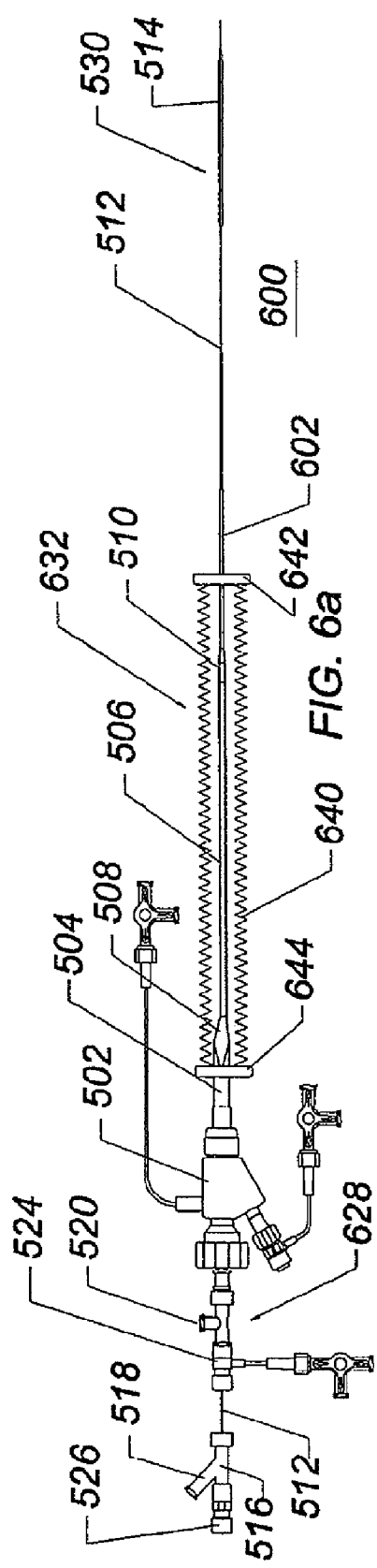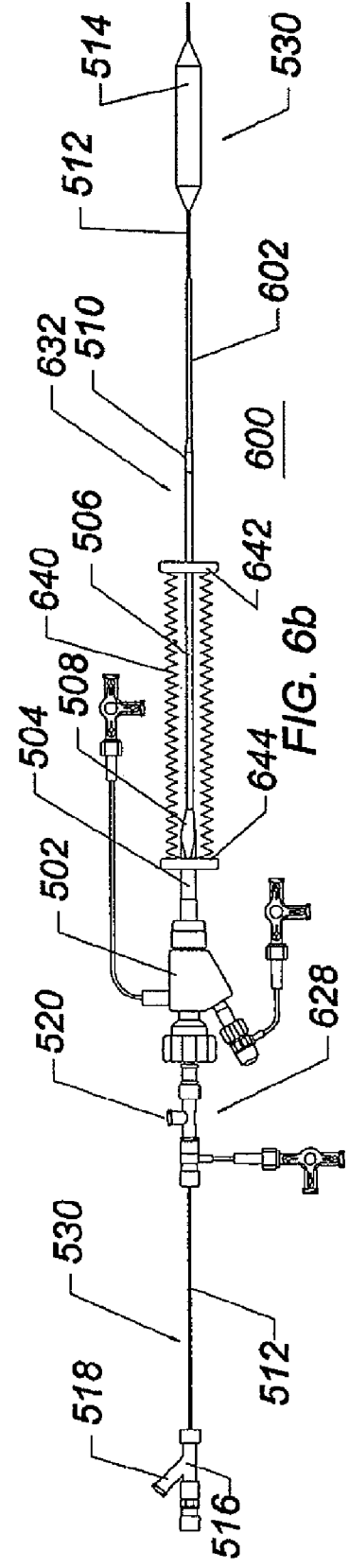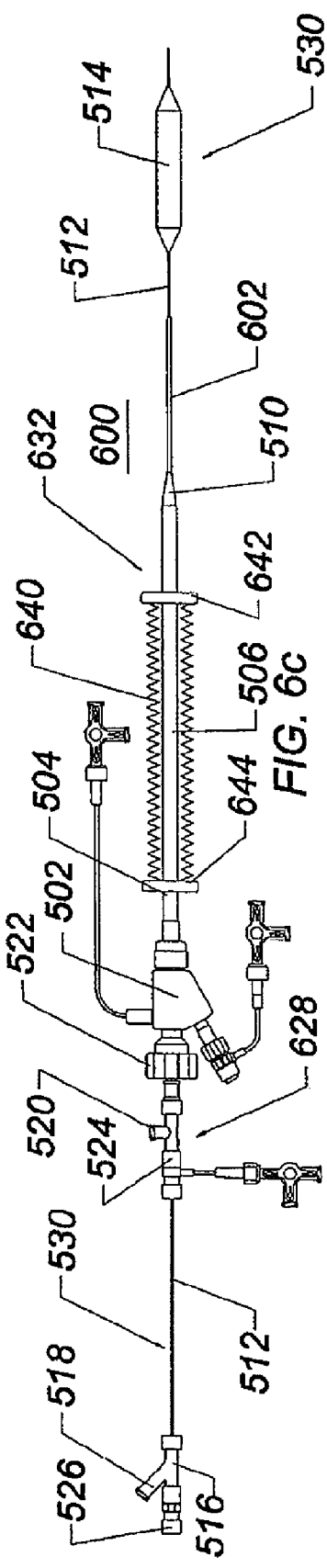

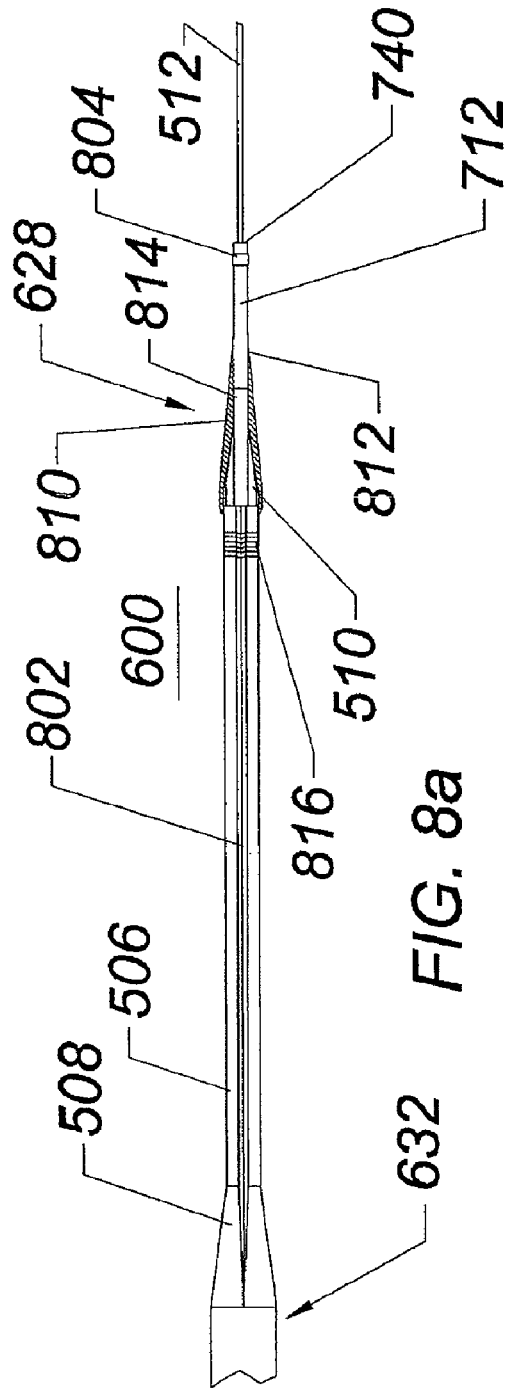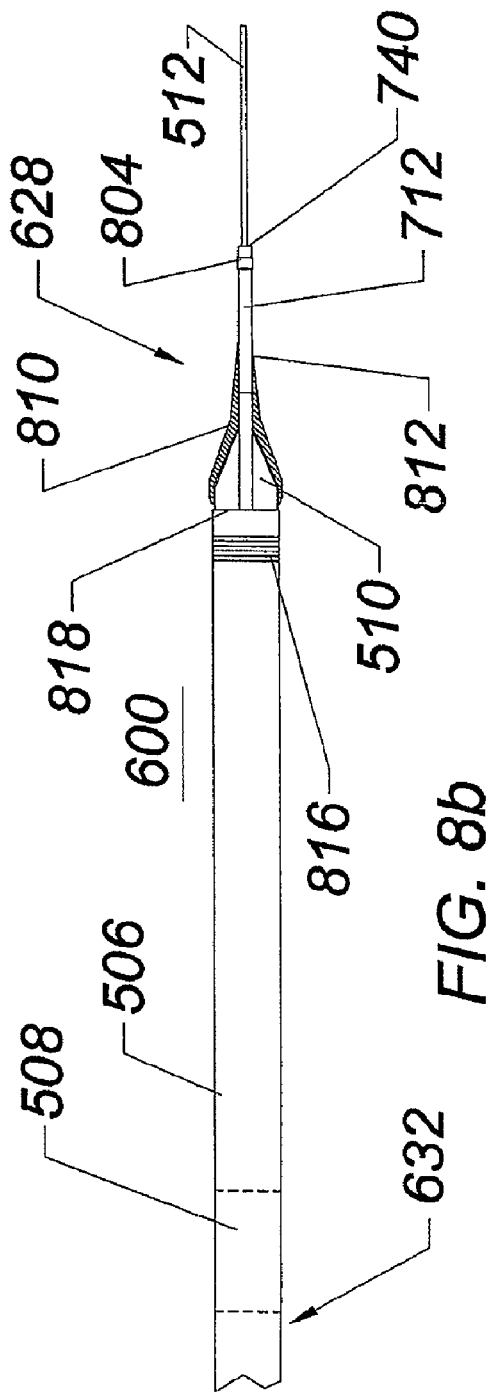

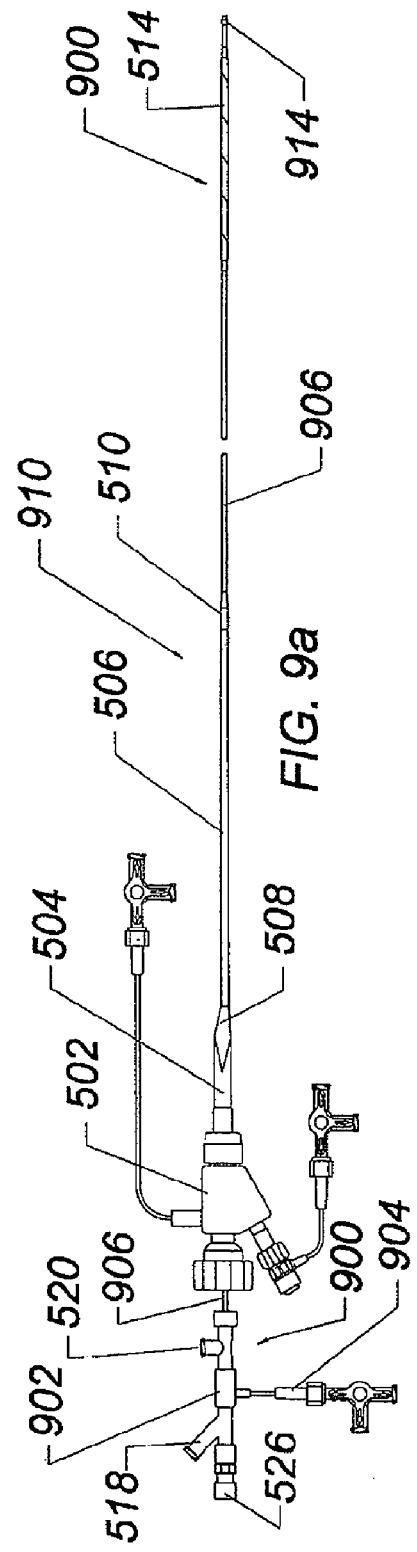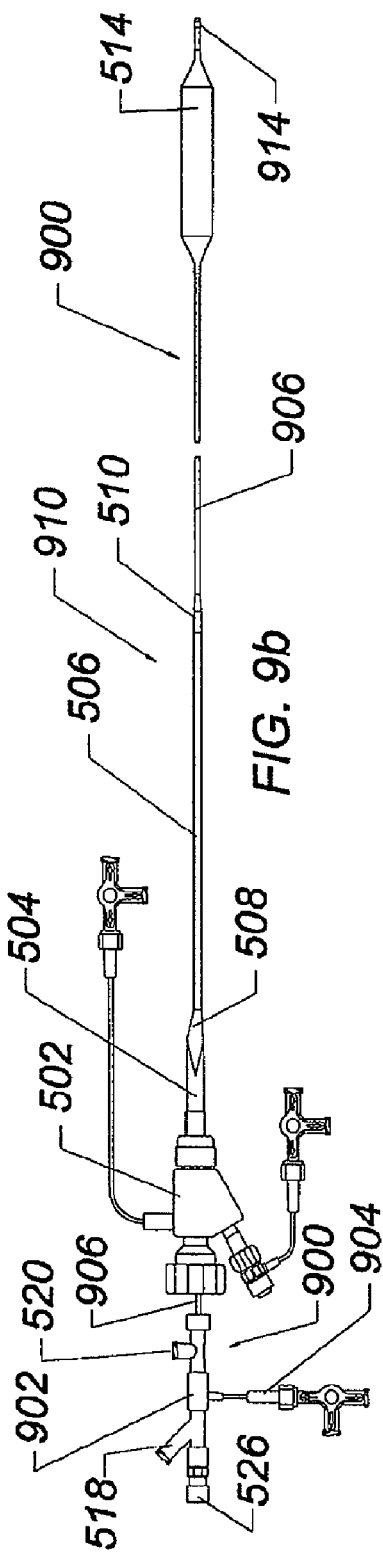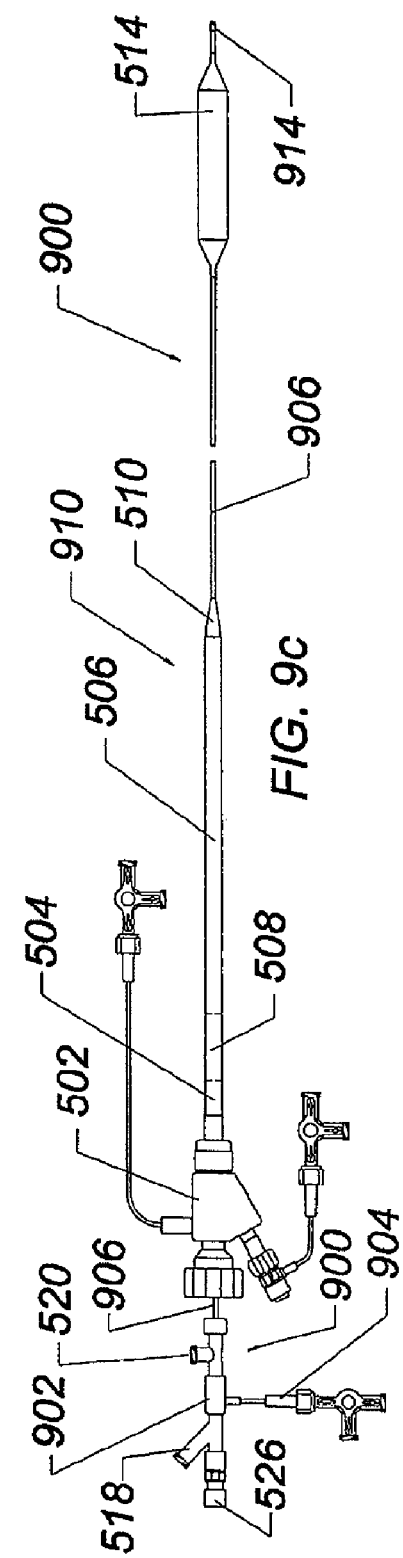

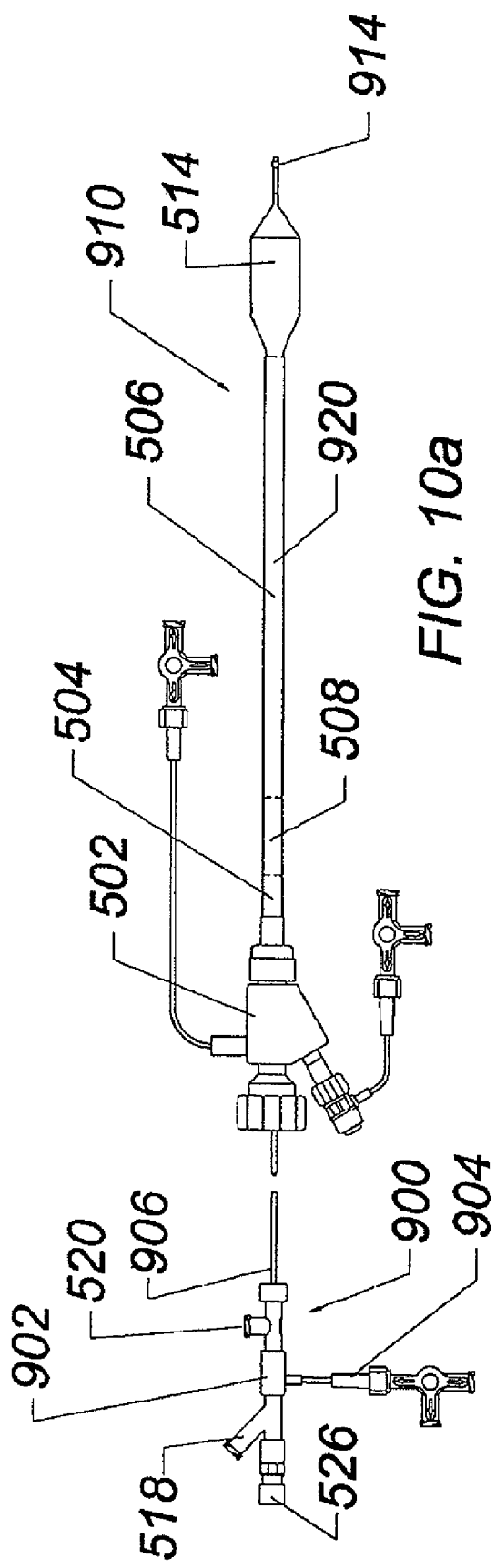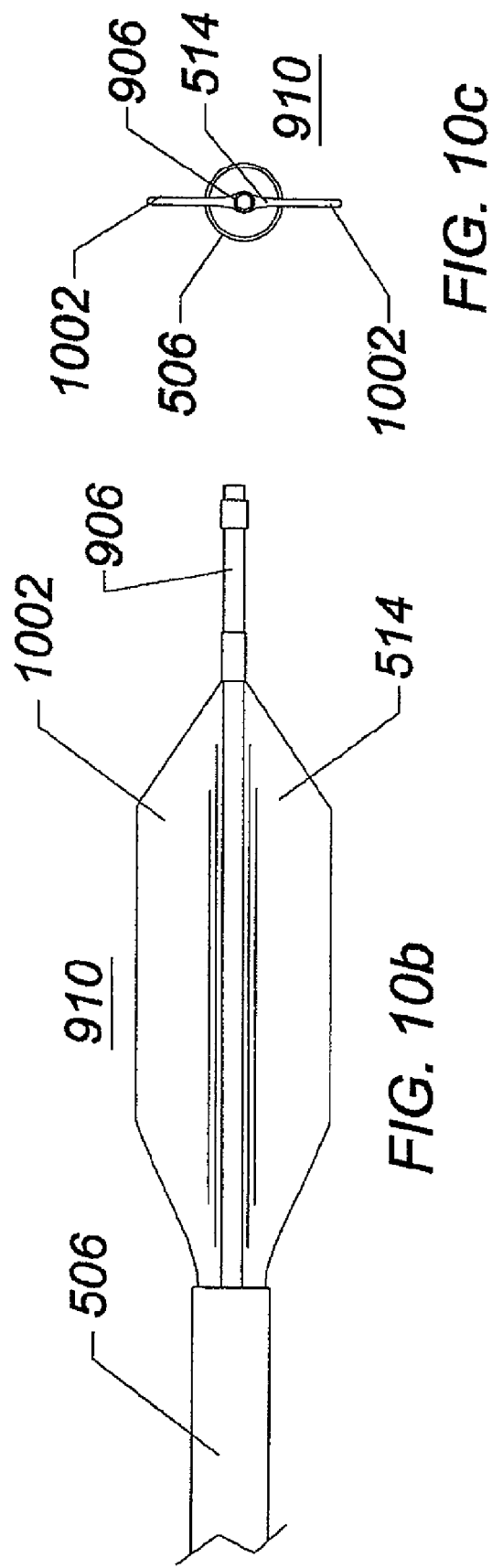

EXPANDABLE INTRA-AORTIC BALLOON PUMP SHEATH

PRIORITY CLAIM

This application claims priority to U.S. Provisional Patent Application Ser. No. 60/887,112, filed on Jan. 29, 2007, titled Expandable Intra-Aortic Balloon Pump Sheath, the entirety of which is hereby incorporated herein by reference.

BACKGROUND OF THE INVENTION

1. Field of the Invention

The invention relates to medical devices for percutaneously accessing body lumens and, more particularly, to methods and devices for accessing the cardiovascular system. In one application, the invention relates to methods and devices for introducing and removing large balloon catheters and instruments, particularly intra-aortic balloon pumps, into and from a patient.

2. Description of the Related Art

A wide variety of diagnostic or therapeutic procedures involves the introduction of a device into the vasculature through a percutaneous incision at an access site. Such regions of the vasculature, preferred for access, include both the arteries and veins, typically at peripheral locations in the body. Typical access sites include the femoral arteries, and the iliac arteries. A percutaneous technique commonly known for such vascular access is the Seldinger technique. The Seldinger technique involves using a hollow needle to puncture the skin and gain access to the selected artery or vein. A guidewire is next placed through the hollow needle into the selected region of vasculature. The guidewire may be advanced to a target location in the vasculature, often more than 100 cm away from the access site. The needle is removed and a tapered dilator with a sheath and a central lumen in the dilator is advanced over the guidewire into the vasculature. The dilator is next removed and a guide catheter is advanced through the sheath over the guidewire. The guide catheter can be advanced all the way, or part way, to the target site. The guide catheter, following, or without, removal of the guidewire can be used for directing therapeutic or diagnostic catheters to regions of the vasculature and central circulation, including external and internal structures of the heart. A general objective of access systems, which have been developed for this purpose, is to minimize the cross-sectional area of the access lumen, while maximizing the available space for the diagnostic or therapeutic catheter placement therethrough. These procedures are especially suited for coronary angioplasty, stent placement, cerebrovascular coil placement, diagnostic cardiac catheterization, cardiac assist, and the like.

One type of cardiac assist procedure involves placement of an intra-aortic balloon pump (IABP) within the descending aorta of a patient and performing counterpulsation within the central circulation. The IABP procedure was originally developed by Dr. Adrian Kantrowitz in the late 1960s for use on surgical patients with the goal of improving coronary perfusion. Today, the procedure involves the steps of inserting a hollow needle, with a hemostasis valve affixed to its proximal end, into the femoral or iliac artery of a patient via a percutaneous puncture. A guidewire is next inserted through the hemostasis valve and the central lumen of the needle into the femoral or iliac artery. The guidewire is routed, under fluoroscopic control, cranially toward the heart until it reaches the aortic arch. The hollow needle is removed from the patient leaving the guidewire in place. A sheath, including a tapered tip central obturator or dilator having a hemostasis valve at its proximal end and further including a central guidewire lumen is routed over the guidewire, through the skin puncture, through the wall of the artery, and into the central lumen of the artery. The central obturator or dilator is removed. An intra-aortic balloon pump catheter is next inserted through the hemostasis valve, through the sheath, and into the artery where it is next advanced to the target site in the thoracic descending aorta. The IABP is operated to support, or augment, the patient's circulation until adequate cardiac function can be restored to allow weaning and removal of the IABP. Indications for IABP use include failure to remove from cardiopulmonary bypass, cardiogenic shock, heart failure, acute myocardial infarct, and support during high-risk interventional procedures such as percutaneous transluminal coronary angioplasty (PTCA), percutaneous heart valve placement, and coronary stent placement. The IABP is connected, at its proximal end, to a pumping and control console. An IABP pumps blood by alternate inflation and deflation within the aorta, using helium gas as the balloon inflation media, while being timed with the opening and closing of the patient's aortic valve so as to provide for optimal circulatory augmentation. Timing of the IABP cycle is generally triggered according to the patient's electrocardiogram, their blood pressure, a pacemaker (if present), or by a pre-set timer. An IABP can achieve as much as a 40% improvement in cardiac output with accompanying reductions in left ventricular stroke work and myocardial oxygen consumption. The IABP can be left in place for periods of hours to more than 2 weeks to allow restoration of natural cardiac function. The IABP can be removed from the patient by first deflating the balloon and then withdrawing the IABP until it is removed from the patient. The sheath is next removed and hemostasis is established using standard techniques for a vessel puncture wound.

Issues can arise, however, when the IABP is removed from the patient. Following deflation, the collapsed balloon, typically fabricated from a thin layer of inelastic polyethylene, may form a plurality of wings, or flattened, radially outwardly projecting structures that are relatively hard and sharp and may not fold neatly against the catheter shaft. Such balloon wings have been reported to cause disruption of vessel plaque during removal or pullback through the aorta, iliac and femoral arteries. This is especially problematic in very sick patients with significant vascular disease that involves plaque, mural thrombus, aneurysms, and other pathologies. The disruption of a region of plaque or thrombus can cause emboli to break free from the vessel wall, float downstream, and lodge within the lumen of smaller distal vessels, blocking blood flow, and resulting in ischemia and possibly tissue necrosis.

Suggested further reading related to the use of intra-aortic balloon pumps includes P. J. Overwalder: "Intra Aortic Balloon Pump (IABP) Counterpulsation", *The Internet Journal of Thoracic and Cardiovascular Surgery*, 1999, Volume 2 Number 2 and "Counterpulsation: Historical Background, Technical Improvements, Hemodynamic and Metabolic Effects", *Cardiology*, Volume 84, 1994, pp. 156-167.

It is desirable to protect the arteries, including the femoral and iliac arteries, from the IABP during removal. A need remains, therefore, for improved access technology, which allows a large diameter balloon catheter to be percutaneously or surgically introduced, endovascularly advanced to the descending aorta, pumped for a period of hours, days, or weeks, and then be removed without causing further injury or complications to the patient.

SUMMARY OF THE INVENTIONS

A transluminal, radially expanding access sheath is provided according to an embodiment of the invention. In an embodiment, the radially expanding sheath, or introducer, is used to provide access to the mammalian aorta by way of a femoral or iliac artery puncture and advancement retrograde toward the aortic arch through the arterial system. The mammalian aorta can be that of a human or human patient. A distal portion of the introducer or sheath is collapsed radially to minimize its outside diameter. A portion of the introducer or sheath, therefore, has a first, smaller cross-sectional profile that can be dilated to a second, larger cross-sectional profile. The catheter, introducer, or sheath can enter a vessel or body lumen with a diameter of 3 to 12 French or smaller, and allow passage of instruments through a central lumen that is 2 to 10 French. At the conclusion of the procedure, the sheath or catheter is capable of gently dilating its entire collapsed length, which can be a small portion of, or substantially the entire working length of the sheath or introducer. The sheath, introducer, or catheter, when expanded, can dilate the arterial puncture site using radially outwardly directed force and permit the removal of instrumentation therethrough, even when that instrumentation is large and unfurled. The sheath or catheter can be maximally visible under fluoroscopy and can be relatively inexpensive to manufacture. The sheath, catheter, or introducer can be kink-resistant and provide a stable or stiff platform for large catheter introduction therethrough.

In an embodiment, the sheath can have an introduction outside diameter that ranges from 3 to 15 French with a preferred range of 5 to 12 French. The inside diameter of the sheath can be expandable to permit instruments ranging up to 30 French to pass therethrough, with a preferred range of between 3 and 20 French. The sheath can have a working length ranging between 20-cm and 200-cm with a preferred length of 50-cm to 150-cm. The expandable distal end of the catheter can comprise between 5% and 95% of the overall working length of the catheter. The outside diameter of the proximal end of the catheter is generally larger than the outside diameter of the expanded distal end, due to increased wall thickness and reinforcement, to provide for pushability, torqueability (preferably approximately 1:1 torqueability), steerability, control, column strength, and the ability to easily pass large diameter instruments therethrough. In an embodiment, the sheath or introducer can be routed to its destination over one or more already placed guidewires with a diameter ranging from 0.010 inches up to 0.050 inches and generally approximating 0.032 to 0.038 inches in diameter.

An embodiment of the invention comprises an endovascular access system further comprising an axially elongate tubular body that defines a lumen extending from the proximal end to the distal end of the sheath. At least a portion of the elongate tubular body is expandable from a first, smaller cross-sectional profile to a second, greater cross-sectional profile. In an embodiment, the first, smaller cross-sectional profile is created by creating axially oriented folds in the sheath material. The expandable region can be the distal end, the proximal end, or both. These folds may be located in only one circumferential position on the sheath, or there may be a plurality of such folds or longitudinally oriented crimps in the sheath. The folds or crimps may be made permanent or semi-permanent by heat-setting the structure, once folded. In an embodiment, a releasable or expandable jacket is carried by the access sheath to restrain at least a portion of the elongate tubular structure in the first, smaller cross-sectional profile during insertion and up to or during inflation of the distal region. In another embodiment, the jacket is replaced by a packaging aid that is removed prior to inserting the sheath into the patient. In an embodiment, the elongate tubular body is sufficiently pliable to allow the passage of objects having a single maximum cross-sectional dimension larger than an inner diameter of the elongate tubular body in the second, greater cross-sectional profile. The adaptability to objects of larger dimension is accomplished by pliability or re-shaping of the cross-section to the larger dimension in one direction accompanied by a reduction in dimension in a lateral direction. The adaptability may also be generated through the use of malleable or elastomerically deformable sheath material. This re-shaping or non-round cross-section can be beneficial in passing two or more catheters through a single sheath with a minimum lateral cross-sectional area.

In another embodiment of the invention, a transluminal access sheath assembly for providing minimally invasive access comprises an elongate tubular member having a proximal end and a distal end and defining a working inner lumen. In this embodiment, the tubular member comprises a folded or creased sheath that can be expanded by a dilatation balloon catheter. The dilatation balloon, affixed to the dilatation balloon catheter, if filled with fluids, preferably liquids and further preferably radiopaque liquids, at appropriate pressure, can generate the necessary force to radially dilate or expand the sheath. The dilatation balloon catheter is removable to permit subsequent instrument or catheter passage through the sheath. The sheath wall can be constructed of malleable materials so that the sheath retains its shape before and after balloon expansion. Such malleable construction can include polymeric walls with metallic coils, braids, meshes, stents, or other reinforcement embedded therein. Longitudinal runners may be disposed within the sheath to serve as tracks for instrumentation, which further minimize friction while minimizing the risk of catching the instrument on the expandable plastic tubular member. Such longitudinal runners are preferably circumferentially affixed within the sheath so as not to shift out of alignment. In yet another embodiment, the longitudinal runners may be replaced by longitudinally oriented ridges and valleys, termed flutes. The flutes, or runners, can be oriented along the longitudinal axis of the sheath, or they can be oriented in a spiral, or rifled, fashion.

In an embodiment, the proximal end of the access assembly, apparatus, or device is preferably fabricated as a structure that is flexible, resistant to kinking, and further retains both column strength and torqueability. Such structures include tubes fabricated with coils or braided reinforcements and preferably comprise inner walls that prevent the reinforcing structures from protruding, poking through, or becoming exposed to the inner lumen of the access apparatus. Such proximal end configurations may be single lumen, or multi-lumen designs, with a main lumen suitable for instrument, guidewire, endoscope, or obturator passage and additional lumens being suitable for control and operational functions such as balloon inflation. Such proximal tube assemblies can be affixed to the proximal end of the distal expandable segments described heretofore.

In an embodiment, the sheath can comprise an inner layer of thin polymeric material, an outer layer of polymeric material, and a central region comprising a coil, braid, stent, plurality of hoops, or other reinforcement. It is beneficial to create a bond between the outer and inner layers at a plurality of points, most preferably at the interstices or perforations in the reinforcement structure, which is generally fenestrated.

Such bonding between the inner and outer layers causes a braided structure to lock in place. In another embodiment, the inner and outer layers are not fused or bonded together in at least some, or all, places. When similar materials are used for the inner and outer layers, the sheath structure can advantageously be fabricated by fusing of the inner and outer layer to create a uniform, non-layered structure surrounding the embedded reinforcement. The polymeric materials used for the outer wall of the jacket are preferably elastomeric to maximize flexibility of the catheter. The polymeric materials used in the composite catheter inner wall may be the same materials as those used for the outer wall, or they may be different. In another embodiment, a composite tubular structure can be co-extruded by extruding a polymeric compound with a stent, braid, or coil structure embedded therein. The reinforcing structure is preferably fabricated from annealed metals, such as fully annealed stainless steel, titanium, or the like. In this embodiment, once expanded, the folds or crimps can be held open by the reinforcement structure embedded within the sheath, wherein the reinforcement structure is malleable but retains sufficient force to overcome any forces imparted by the sheath tubing.

In an embodiment, the sheath is inserted into the patient in its collapsed configuration. In this embodiment, a therapeutic balloon catheter is pre-inserted through the collapsed central lumen of the sheath so that the therapeutic balloon projects distally of the collapsed expandable region of the introducer. The therapeutic balloon catheter, which comprises the large diameter balloon, also comprises inflation lumens allowing for pulsatile, repeated inflation-deflation cycles of the large diameter balloon such as found in an intra aortic balloon pump. The therapeutic balloon catheter can comprise a secondary sheath expansion device such as a coaxially-mounted angioplasty-type balloon that is furled and can be inserted inside the collapsed, non-expanded sheath. The introducer, or its dilator, can comprise a lead in sheath, which is small in diameter and passes percutaneously into the vasculature during the majority of the time during which the therapeutic balloon catheter functions. Following completion of the therapy, an example of which is intra-aortic balloon counterpulsation, the lead in sheath is either split and peeled away, or advanced with the dilator to introduce the expandable portion of the sheath into the patient's vasculature. Following operation of the intra aortic balloon pump, the large diameter balloon is deflated and the secondary sheath expansion device is activated to expand the sheath to a large diameter. The secondary sheath expansion device, which can be a balloon, is deactivated or deflated and the entire therapeutic balloon catheter can now be safely withdrawn within the sheath and removed from the patient without concern for the edges of the deflated large diameter balloon coming in contact with the patient's vessel walls. The sheath can now be removed from the patient either fully expanded or following collapse of the expandable region.

In an embodiment of the invention, it is beneficial that the sheath comprise a radiopaque marker or markers. The radiopaque markers may be affixed to the non-expandable portion or they may be affixed to the expandable portion. Markers affixed to the radially expandable portion preferably do not restrain the sheath or catheter from radial expansion or collapse. Markers affixed to the non-expandable portion, such as the catheter shaft of a balloon dilator can be simple rings that are not radially expandable. Radiopaque markers include shapes fabricated from malleable material such as gold, platinum, tantalum, platinum-iridium, and the like. Radiopacity can also be increased by vapor deposition coating or plating metal parts of the catheter with metals or alloys of gold, platinum, tantalum, platinum-iridium, and the like. Expandable markers may be fabricated as undulated or wavy rings, bendable wire wound circumferentially around the sheath, or other structures such as are found commonly on stents, grafts, stent-grafts, or catheters used for endovascular access in the body. Expandable radiopaque structures may also include disconnected or incomplete surround shapes affixed to the surface of a sleeve or other expandable shape. Non-expandable structures include circular rings, bands, cylinders, or other structures that completely surround the catheter circumferentially and are strong enough to resist expansion. In another embodiment, the polymeric materials of the catheter or sheath may be loaded with radiopaque filler materials such as, but not limited to, bismuth salts, or barium salts, or the like, at percentages ranging from 1% to 50% by weight in order to increase radiopacity. The radiopaque markers allow the sheath to be guided and monitored using fluoroscopy.

In order to enable radial or circumferential expansive translation of the reinforcement, it may be beneficial not to completely bond the inner and outer layers together, thus allowing for some motion of the reinforcement in translation as well as the normal circumferential expansion. Regions of non-bonding may be created by selective bonding between the two layers or by creating non-bonding regions using a slip layer fabricated from polymers, ceramics or metals. Radial expansion capabilities are important because the proximal end needs to transition to the distal expansive end and, to minimize manufacturing costs, the same catheter may be employed at both the proximal and distal end, with the expansive distal end undergoing secondary operations to permit radial, or diametric, expansion.

In another embodiment, the distal end of the catheter is fabricated using an inner tubular layer, which is thin and lubricious. This inner layer is fabricated from materials such as, but not limited to, FEP, PTFE, polyamide, polyethylene, polypropylene, Pebax, Hytrel, and the like. The reinforcement layer comprises a coil, braid, stent, or plurality of expandable, foldable, or collapsible rings, which are generally malleable and maintain their shape once deformed. Preferred materials for fabricating the reinforcement layer include but are not limited to, stainless steel, tantalum, gold, platinum, platinum-iridium, titanium, nitinol, and the like. The materials are preferably fully annealed or, in the case of nitinol, fully martensitic. The outer layer is fabricated from materials such as, but not limited to, FEP, PTFE, polyamide, polyethylene, polypropylene, polyurethane, Pebax, Hytrel, and the like. The inner layer is fused or bonded to the outer layer through holes in the reinforcement layer to create a composite unitary structure. The structure is crimped radially inward to a reduced cross-sectional area. A balloon dilator is inserted into the structure before crimping or after an initial crimping and before a final sheath crimping. The balloon dilator is capable of forced radial, or diametric, expansion of the reinforcement layer, which provides sufficient strength necessary to overcome any forces imparted by the polymeric tubing, thus controlling the cross-sectional shape of the polymeric tubing. The dilator is also capable of overcoming any forces imparted by tissues, including atrial or even ventricular myocardial tissue, through which the sheath is inserted.

Another embodiment of the invention comprises a method of providing endovascular protection for vascular or arterial structures through which an intra-aortic balloon pump catheter is passed. The method first comprises percutaneously placing a hollow needle into the femoral artery, inserting a guidewire through the hollow needle into the artery, withdrawing the hollow needle, and inserting a sheath with a tapered obturator into the puncture site and into the artery over the guidewire. The guidewire is next withdrawn, as is the tapered obturator and a 0.032 to 0.038-inch guidewire, preferably a stiff or super-stiff guidewire, is advanced into the artery and approximately to the level of the aortic arch. The IABP catheter, having a shaft that is 5 to 10 French in diameter, pre-inserted within the lumen of a radially expandable sheath is next advanced into the femoral artery and advanced to the top of the descending aorta over the guidewire. The guidewire is optionally withdrawn or it may be retained in place. The expandable sheath is maintained collapsed and in position just proximal to the balloon of the IABP. The IABP is operated for a period of hours to weeks, wherein the large diameter balloon, which is 20 to 40 mm diameter, is repeatedly expanded and collapsed, under fluid pressure, to cause volumetric change within the aorta, in synchronization with the patient's heart. Such expansion and contraction cycles can occur at a rate of between 40 and 200 beats per minute. A sheath dilator, positioned within the expandable sheath and optionally integral to the IABP catheter shaft, is next radially expanded, forcefully causing the sheath, or its distal end, to expand radially so as to dilate the expandable portion of the sheath. The dilator is next deflated along with the IABP balloon and the entire assembly is removed from the sheath. Alternatively, the IABP balloon catheter is withdrawn sufficiently to shield the collapsed IABP balloon from the blood vessel walls. The sheath is configured to re-fold or compress the IABP balloon prior to removal so that when the IABP balloon is pulled out of the arteries, the artery walls are protected. Suitable hemostatic and anti-reflux valves and seals are affixed the distal end of all devices except guidewires to ensure maintenance of hemostasis and prevention of air entry into the vasculature. Following therapeutic or diagnostic procedures, or both, the sheath is withdrawn from the patient allowing the arterial puncture to close.

The expandable access sheath is configured, or tailored, to bend, or flex, around vascular tortuosity and be advanced into the aorta through potentially tortuous iliac and femoral arteries. Provision can optionally be made to actively orient or steer the sheath through the appropriate angles of between 20 to 120 degrees or more and to bend in one or even two planes of motion. The steering mechanism, in various embodiments, can be a curved guidewire and straight catheter, curved catheter and straight guidewire, a movable core guidewire, or a combination of the aforementioned. In one embodiment, radial expansion of the distal end of the access sheath from a first, smaller diameter cross-section to a second larger diameter cross-section is next performed, using a balloon dilator. The balloon dilator is subsequently removed from the sheath to permit passage of instruments that may not normally have been able to be inserted into the vasculature. Once the sheath is in place, the guidewire may be removed or, in another embodiment, it may be left in place.

In another embodiment of the invention, the expandable sheath is not pre-mounted to the therapeutic balloon catheter. Instead, the expandable sheath is configured so that it retains an internal lumen, even in its collapsed, first smaller cross-sectional configuration, such that the therapeutic balloon catheter can be inserted therethrough. In this embodiment, the collapsed sheath is inserted into the circulatory system with a central obturator and nose cone over a guidewire. The obturator is removed and the therapeutic balloon catheter is inserted through the collapsed sheath and into the circulatory system. The therapeutic balloon catheter is cyclically inflated and deflated for a period of time, following which it is finally deflated. A sheath dilation catheter is next inserted into the collapsed portion of the sheath. The sheath dilatation catheter is inflated to expand the first, smaller cross-sectional area to a second, larger cross-sectional area. The sheath dilatation catheter is deflated and removed from the sheath, following which the deflated therapeutic balloon catheter is withdrawn into the sheath so that it is shielded from outside tissue. The entire sheath is next removed from the patient, with or without the therapeutic balloon catheter having been entirely removed from the expandable sheath.

In another embodiment of the invention, the proximal end of the expandable sheath comprises hemostasis or backflow check seals or valves to prevent blood loss and retrograde flow of air into the circulatory system. The hub of the sheath comprises such a hemostasis seal. The seal comprises an annular soft elastomeric gasket that seals against catheters, instruments, and the dilator, inserted therethrough. The seal can further comprise a valve such as a stopcock, a hemostasis valve, a one-way valve such as a duckbill or flap valve, or the like to prevent significant blood loss and air entry when an instrument or catheter is removed from the lumen of the expandable sheath. The soft annular seal can further comprise a mechanism to compress the inner diameter of the seal radially inward, such as the mechanisms found on Tuohy-Borst valves. The hub further comprises one or more sideport for injection of contrast media such as Omnipaque®, Renografin®, or other Barium-loaded solutions, for example, saline, or anticoagulant solutions such as warfarin, heparin, Coumadin®, persantin, or the like, or for the measurement of pressure at or near the distal end of the sheath. The dilator hub comprises a central lumen with a Tuohy-Borst valve and one or more sideports for balloon inflation, said sideports operably connected to lumens in the dilator catheter for injection or withdrawal of fluids from a balloon at the distal end of the dilator and optionally for measurement of pressure at or near the dilator distal end. The dilator hub, the sheath hub, or both, can also comprise a handle, lever, or trigger mechanism to enable steering mechanisms at the distal end of the dilator, the sheath, or both, respectively.

The expandable sheath, in an embodiment, comprises radiopaque markers to denote the beginning, and end, of the expandable region and the middle of the expandable region. The middle of the expandable region is useful in that it can be aligned with the atrial septum during the sheath expansion procedure. The sheath can comprise radiopaque materials such as gold wire, platinum wire, tantalum wire, or coatings of the aforementioned over a malleable, stainless steel, deformable reinforcing layer. Such complete radiopaque markings are especially useful for sheath dilation insofar as they allow the operator to more clearly visualize the extent to which the sheath has been dilated once the dilator is activated. In a preferred embodiment, a radiopaque marker band is affixed to the dilator substantially near the distal tip of the dilator so that the position of the distal tip can be observed and controlled relative to the wall of the aorta or other cardiac structures. This radiopaque marker band can be a non-expandable, axially elongate tubular structure that is adhered to the non-expandable dilator shaft. Another non-expandable radiopaque marker band can be adhered to the dilator shaft at a position substantially corresponding to the proximal most dilating portion of the dilator or sheath. Another non-expandable radiopaque marker band can be adhered to the dilator shaft at a position substantially corresponding to the distal most dilating portion of the dilator or sheath. The radiopaque marker bands can further be configured to appear different under fluoroscopy, for example by making the distal tip marker a single band, the distal dilation marker two bands, and the proximal dilator marker, three bands. Yet another configuration of radiopaque marker bands can be achieved by using malleable wire windings of gold, tantalum, platinum alloys, or the like, which are embedded within the folded and expandable sheath, preferably at or near the distal end of the sheath and, optionally, at or near the proximal end of the expandable portion of the sheath. These wire windings can expand with the sheath and can help show the extents of the sheath even after the dilator has been removed.

In an embodiment, the sheath dilator or expander is a separate catheter from the therapeutic or diagnostic catheter and which can be removed or advanced separately from the therapeutic or diagnostic catheter. In another embodiment, the sheath dilator is affixed to or integral to the therapeutic or diagnostic catheter. In this latter embodiment, the sheath dilator can be an angioplasty-type, non-elastomeric balloon affixed to the therapeutic or diagnostic catheter at a location proximal to the therapeutic or diagnostic mechanisms at the distal end of the catheter. The inflation lumen for the sheath expansion dilator balloon is separate from that of the inflation lumen for the therapeutic or diagnostic device at the distal end of the catheter. These sheath expansion lumen and the therapeutic working lumen can run the length of the catheter and are operably connected to and generally terminate at ports at the proximal end of the catheter, for example on a hub, Y-connector, or other structure. At its distal end, the sheath expansion lumen is operably connected with the interior volume of the sheath expansion balloon. The sheath expansion lumen does not continue to and vent from the distal end of the catheter. The therapeutic working lumen or therapeutic balloon inflation lumen generally terminates at, and is operably connected with, the volume described by the interior of the therapeutic balloon. In an exemplary case, the therapeutic or diagnostic balloon is an intra-aortic balloon pump.

In another embodiment, the proximal end of the sheath comprises a non-circular interior cross-section. The interior cross-section of the sheath can be oval, or it can comprise two or more completely walled off or partially walled off separate lumens. The sheath hub, which is affixed to the non-expandable proximal end of the sheath, can comprise two or more separate instrumentation ports, each of which are operably connected to a lumen or partial lumen within the sheath and which can advantageously comprise hemostasis valves, sealing gaskets, or the like. The instrumentation ports are especially useful for passage of, for example, multiple catheters. Segregation of the multiple catheters can be useful to prevent binding or interference between the multiple catheters or instruments passed through the sheath. In yet another embodiment, the proximal end of the sheath has a non-circular cross-section that minimizes the overall cross-sectional area or circumference of a sheath configured to accept two or more catheters. This non-circular cross-section can be an oval, ellipse, rounded triangle, or the like. The non-circular cross section can, for example, reduce an 18 French OD catheter to around 15.5 French, using the same wall thickness and still retain the capability to accept two 8 French catheters within its internal lumen or lumens. Reduction in exterior cross-section is clearly useful in making the procedure as minimally invasive as possible and may make a procedure, which normally takes a cutdown, a percutaneous procedure.

In another embodiment, the guidewire port on the dilator hub is operably connected to a sideport. The sideport further comprises a flexible line and a luer connector and may further comprise an optional stopcock or one way valve. The sideport can be a T-fitting, a Y-fitting, or it can be integrally molded with the guidewire port on the dilator hub. The sideport can accept catheters or instruments for the purpose of, for example, taking pressure or flow rate measurements. The guidewire port is preferably terminated at its proximal end with a Tuohy-Borst fitting, hemostasis valve, ring gasket, or other valve or seal system. In yet another embodiment, the exterior of the sheath, and optionally the internal lumen of the sheath, can be coated with a lubricious coating comprising materials such as, but not limited to, silicone oil or a hydrophilic hydrogel. The dilator hub can further comprise one or more irrigation, aspiration, or purge port operably connected to the guidewire lumen and preferably terminated with a stopcock. Such irrigation, aspiration, or purge port can also be affixed to the sheath hub and be operably connected to the central lumen of the expandable sheath. In yet another embodiment, the expandable sheath can comprise an outer sleeve which surrounds the sheath and dilator and provides an aseptic barrier during the insertion and therapeutic function of the central catheter, such therapeutic function including, but not limited to, intra-aortic balloon counterpulsation. The outer sleeve can further comprise seals at one or both ends to facilitate sheath or catheter function while maximizing the protective function of the outer sleeve.

For purposes of summarizing the invention, certain aspects, advantages and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein. These and other objects and advantages of the present invention will be more apparent from the following description taken in conjunction with the accompanying drawings.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention. Throughout the drawings, reference numbers are re-used to indicate correspondence between referenced elements.

FIG. 5a is a lateral side view of an uninflated IABP catheter, wherein the IABP is pre-inserted through a collapsed, expandable sheath, according to an embodiment of the invention;

FIG. 5b is a lateral side view of an IABP, wherein the distal region of the sheath has been diametrically expanded and the IABP balloon is fully inflated, according to an embodiment of the invention;

FIG. 5c is a lateral side view of an IABP, wherein the deflated IABP balloon is being withdrawn proximally into the expanded distal region of the sheath, according to an embodiment of the invention;

FIG. 6a is a side view illustration of an IABP system, wherein an IABP catheter is inserted through a collapsed, expandable sheath and dilator and a small diameter lead-in sheath, according to an embodiment of the invention;

FIG. 6b illustrates a side view of the IABP system of FIG. 6a, wherein the unexpanded, collapsed, expandable sheath, dilator, and small diameter lead-in sheath have been advanced distally toward the IABP balloon, according to an embodiment of the invention;

FIG. 6c illustrates a side view of the IABP system of FIG. 6b wherein the IABP catheter balloon is shown expanded and the expandable sheath has been expanded by the dilator, according to an embodiment of the invention;

FIG. 8a is a side view illustration of the distal end of the radially collapsed IABP sheath system with the fairing tip on the dilator being shown in cross-section, according to an embodiment of the invention;

FIG. 8b is a side view illustration of the distal end of the radially dilated IABP sheath system with the dilator still in place and the fairing tip being shown in cross-section, according to an embodiment of the invention;

FIG. 9a is a side view illustration of an IABP sheath system wherein the sheath dilator is integral to the IABP catheter, according to an embodiment of the invention;

FIG. 9b is a side view illustration of the IABP sheath system of FIG. 9a wherein the dilator balloon remains unexpanded but the IABP pumping balloon is shown in its inflated state, according to an embodiment of the invention;

FIG. 9c illustrates a side view of the IABP sheath system of FIGS. 9a and 9b wherein the dilator balloon is inflated and the expandable distal region of the sheath is expanded diametrically to its second, enlarged configuration, according to an embodiment of the invention;

FIG. 10a illustrates a side view of the IABP sheath system of FIG. 9c wherein the dilator balloon and the IABP balloon have both been deflated. The IABP balloon and catheter are being withdrawn into the expanded sheath, according to an embodiment of the invention;

FIG. 10b illustrates an enlarged side view of the IABP sheath system of FIG. 10a, according to an embodiment of the invention; and FIG. 10c illustrates front view of the IABP sheath system following deflation of the dilator balloon and the IABP balloon, according to an embodiment of the invention.

DETAILED DESCRIPTION OF THE PREFERRED EMBODIMENTS

The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

The invention, which can be generally termed a catheter or a sheath, can be described as being an axially elongate hollow tubular structure having a proximal end and a distal end. The axially elongate structure further has a longitudinal axis and has an internal through lumen that extends from the proximal end to the distal end for the passage of instruments, fluids, tissue, or other materials. The axially elongate hollow tubular structure is generally flexible and capable of bending, to a greater or lesser degree, through one or more arcs in one or more directions perpendicular to the main longitudinal axis. As is commonly used in the art of medical devices, the proximal end of the device is the end that is closest to the user, typically a cardiologist, surgeon, or electrophysiologist. The distal end of the device is the end closest to the patient or that is first inserted into the patient. A direction being described as being proximal to a certain landmark will be closer to the user, along the longitudinal axis, and further from the patient than the specified landmark. The diameter of a catheter is often measured in "French Size" which can be defined as 3 times the diameter in millimeters (mm). For example, a 15 French catheter is 5 mm in diameter. The French size is designed to approximate the circumference of the catheter in mm and is often useful for catheters that have non-circular cross-sectional configurations. While the original measurement of "French" used π (3.14159 . . . ) as the conversion factor between diameters in millimeters (mm) and French, the system has evolved today to where the conversion factor is 3.0.

Figure 1:
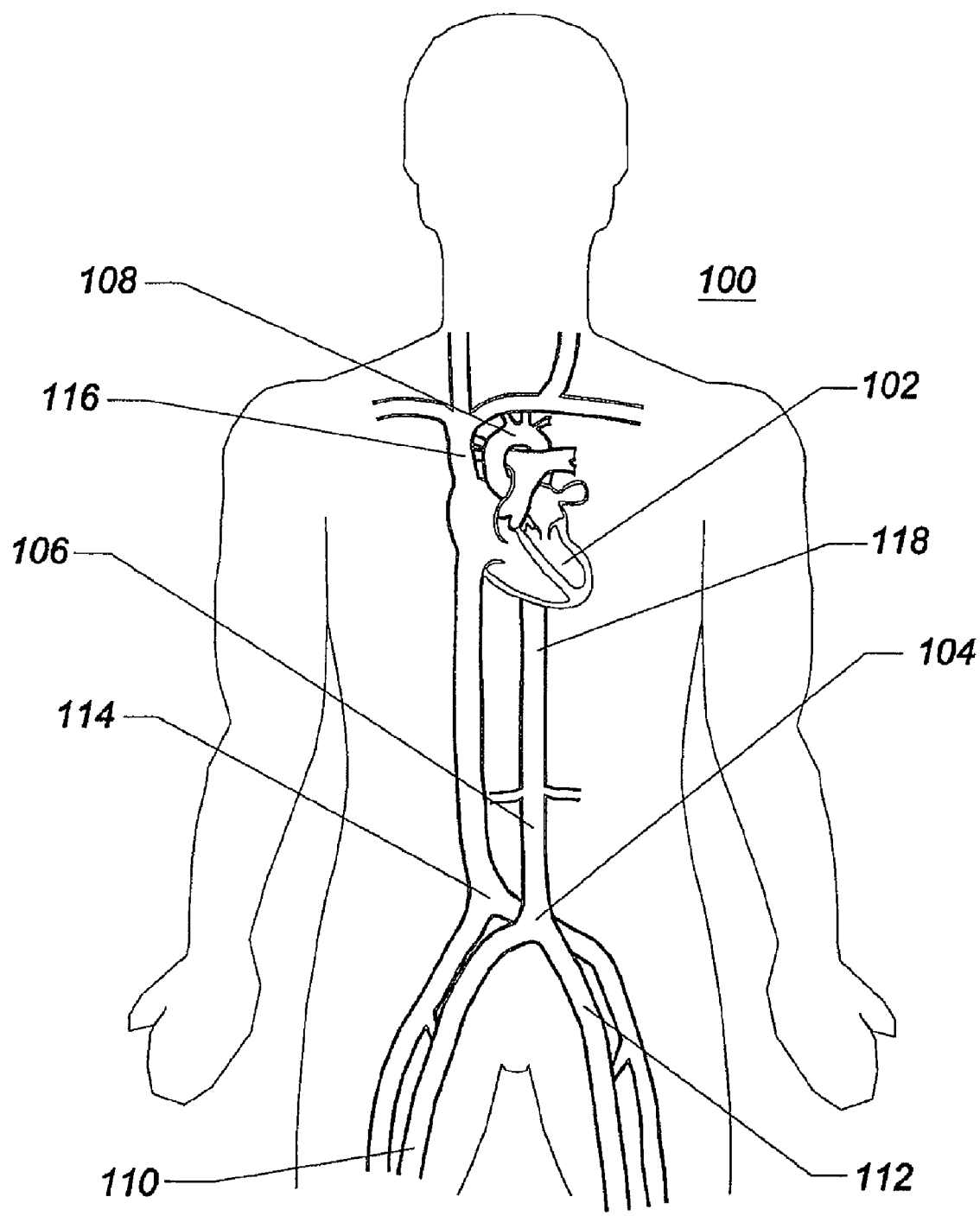
FIG. 1 is a front view schematic representation of the human circulatory system including the heart, the aorta, the iliac and femoral arteries.

FIG. 1 is a schematic frontal (anterior) illustration (looking posteriorly) of a human patient 100 comprising a heart 102, an aortic bifurcation 104, a descending aorta 106, an aortic arch 108, an inferior vena cava 114, a superior vena cava 116, an iliac artery 112, a femoral artery 110, and a thoracic aorta 118. In this illustration, the left anatomical side of the body of the patient 100 is toward the right of the illustration. FIG. 1 primarily illustrates components of the central circulation.

Referring to FIG. 1, the heart 102 is a pump, the outlet of which is the aorta, including the aortic arch 108, the thoracic aorta 118, the descending aorta 106, and the aortic bifurcation 104, which comprise the primary artery in the systemic circulation. The circulatory system, which is operably connected to the heart 102 further comprises the return, or venous, circulation. The venous circulation comprises the superior vena cava 116 and the inferior vena cava 114, which return blood from the upper extremities and lower extremities, respectively. The iliac arteries 112 are operably connected to, and receive blood from, the aortic bifurcation 104. The femoral arteries 110, are operably connected to, and receive blood from, the iliac arteries 112. The veins, which terminate in the superior vena cava 116 and the inferior vena cava 114, carry blood from the tissues of the body back to the right heart, which then pumps the blood through the lungs and back into the left heart. Pressures within the venous circulation generally average 20 mm Hg or less. The arteries of the circulatory system carry oxygenated blood (not shown) from left ventricle of the heart 102 to the tissues of the body 100. The pressures within the aorta undulate, with a modified triangle waveform, between a diastolic pressure of around 80 mm Hg to a systolic pressure of around 120 mm Hg. A hypotensive person may have arterial pressure lower than 120/80 mm Hg and a hypertensive person may have arterial pressures higher than 120/80 mm Hg. Systolic arterial pressures of 300 mm Hg can occur in extremely hypertensive persons.

Figure 2:
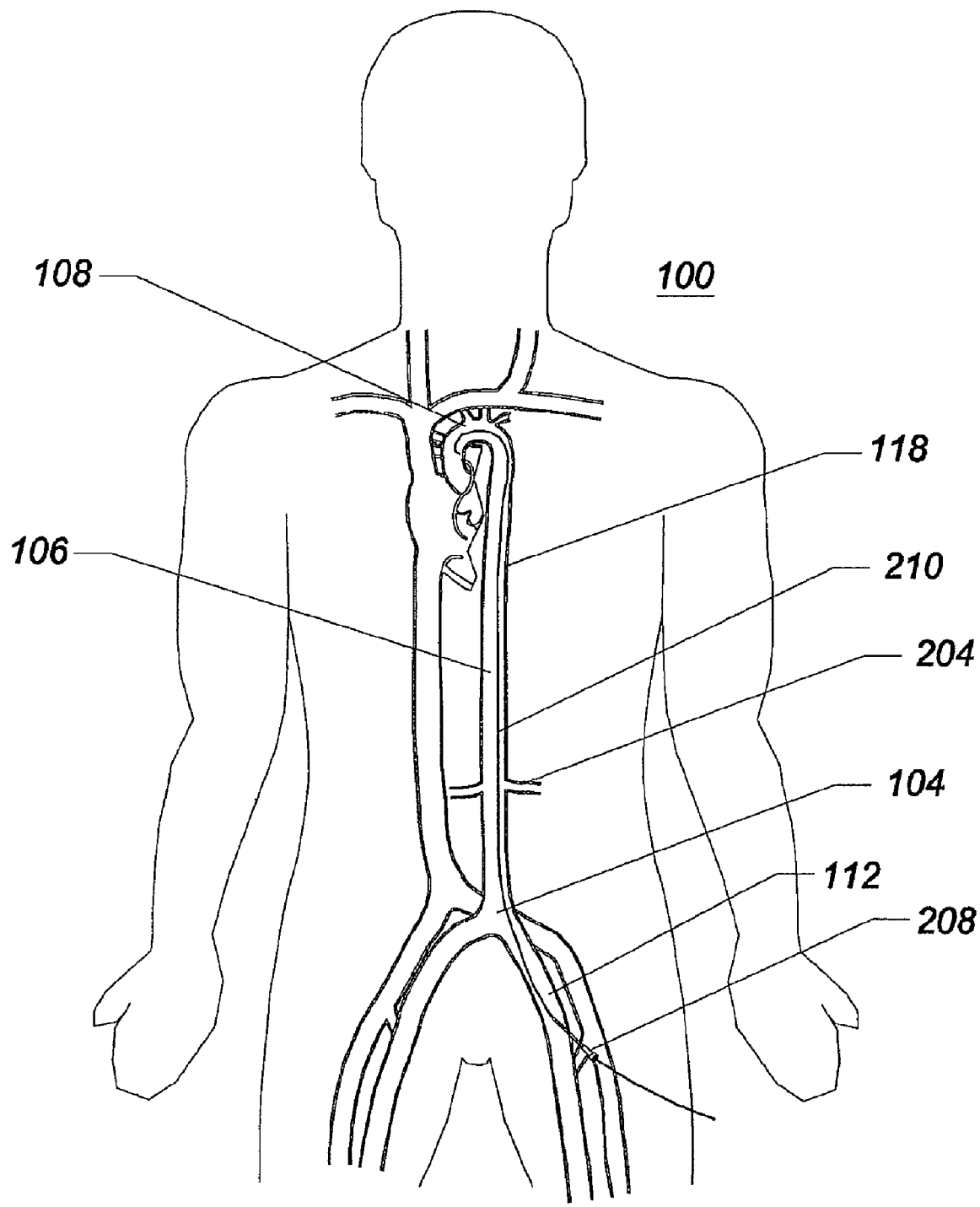
FIG. 2 is a front view schematic representation of the human circulatory system with a guidewire routed from the femoral artery into the aorta, according to an embodiment of the invention.

FIG. 2 is a schematic frontal illustration, looking posteriorly from the anterior side, of the patient 100. In this illustration, much of the right ventricle, left ventricle, and left atrium have been cut away to permit visibility of the thoracic aortic structure 118, which lies posterior to the heart 102. A vascular introduction sheath 208 has been inserted into the left iliac artery 112 via a percutaneous puncture or incision. A guidewire 210 has been inserted through the introduction sheath 208 and routed, cranially, through the aortic bifurcation 104, up the descending aorta 106 past the renal arteries 204, through the thoracic aorta 118, and into the aortic arch 108. In this illustration, the left anatomical side of the patient 100 is toward the right. The guidewire 210 has been placed so that it can be used to track therapeutic or diagnostic catheters into a region of the thoracic aorta 118.

Referring to FIG. 2, The central arterial circulation, through which the guidewire 210 has been routed, may range from 60 to over 300 mm Hg depending on the level of hypertension or hypotension existent in the patient. By accessing the heart through the arterial circulation, the chance of hemorrhage from the catheter insertion site is minimized by use of hemostasis valves built into any catheters, sheaths, or introducers 208 used on the patient. The guidewire 210 is generally of sufficient length that the portion of it that extends outside the body and the introducer 208 is long enough to be inserted through the guidewire lumen of a catheter capable of accessing near the end of the guidewire while the guidewire projects out the proximal end of the catheter. Thus, the guidewire is as long as, or longer than, twice the distance to the treatment site in the patient 100. The ideal guidewire diameter ranges from about 0.032 inches to about 0.038 inches or larger. Guidewires can be PTFE coated to improve lubricity and can have various types of tip configurations including, but not limited to, straight, "J", floppy tip, rigid tip, and the like. Access, in this illustration is gained through the iliac artery 112 but, if the catheters are small enough, the access can be gained through a femoral artery 110.

Figure 3:
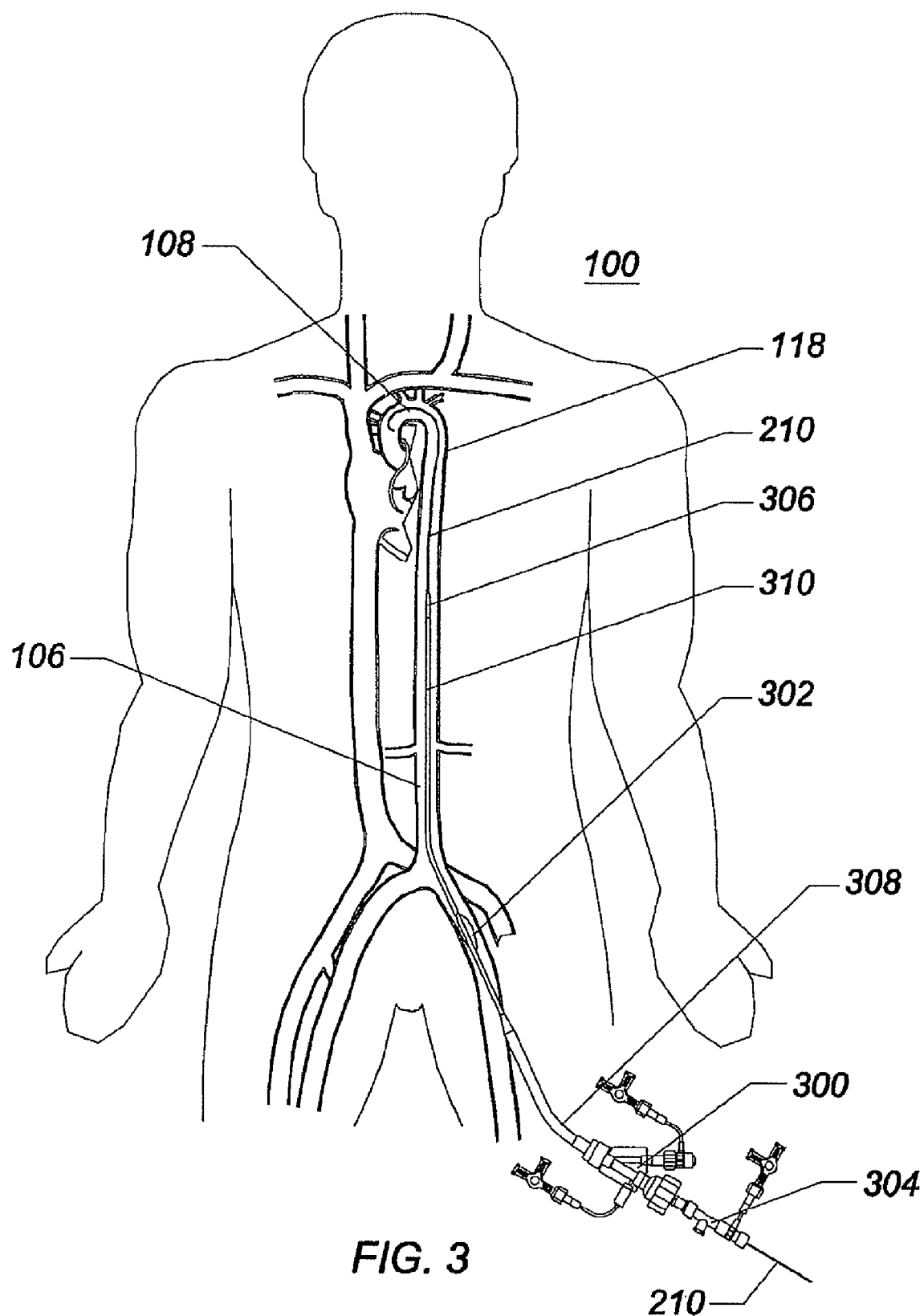
FIG. 3 is a front view schematic representation of the human circulatory system with an expandable sheath advanced into the aorta, according to an embodiment of the invention.

FIG. 3 is a frontal illustration, looking posteriorly from the anterior side, of the patient 100. The vascular introducer 208, shown in FIG. 2, has been removed from the left iliac artery 112 and a larger Trans-Septal Expandable Sheath 300 has been inserted into the arterial circulation through the percutaneous puncture or surgical incision 302 over the guidewire 210 and routed through the descending aorta 106 into the thoracic aorta 118. The expandable trans-septal sheath 300 comprises a dilator 304, the proximal most part of which is illustrated in FIG. 3. The dilator 304 of the expandable trans-septal sheath 300 further comprises a dilator tip fairing 306. The expandable sheath 300 further comprises a proximal non-expandable region 308, and a distal expandable region 310. In another embodiment, the entire working length of the sheath 300 could comprise the expandable region 310. The working length of a sheath or catheter 300 is that part that projects distally of the hub or any enlargements associated therewith.

Referring to FIG. 3, the systemic, arterial circulation is filled with blood (not shown) that is oxygenated and on its way to be delivered to the body tissues. In the illustrated embodiment, the expandable region 310 of the expandable trans-septal sheath 300 is smaller in diameter than the proximal non-expandable region 308. The expandable sheath 300 further comprises, at its proximal end, a plurality of ports on the hub that access the central lumen of the sheath. The dilator 304 similarly has a plurality of ports on its hub. The dilator ports are not operably connected together, but rather are connected to separate lumens or annuli disposed within the dilator 304 to facilitate such functions as guidewire passage, pressure measurement, or balloon expansion and deflation.

Figure 4:
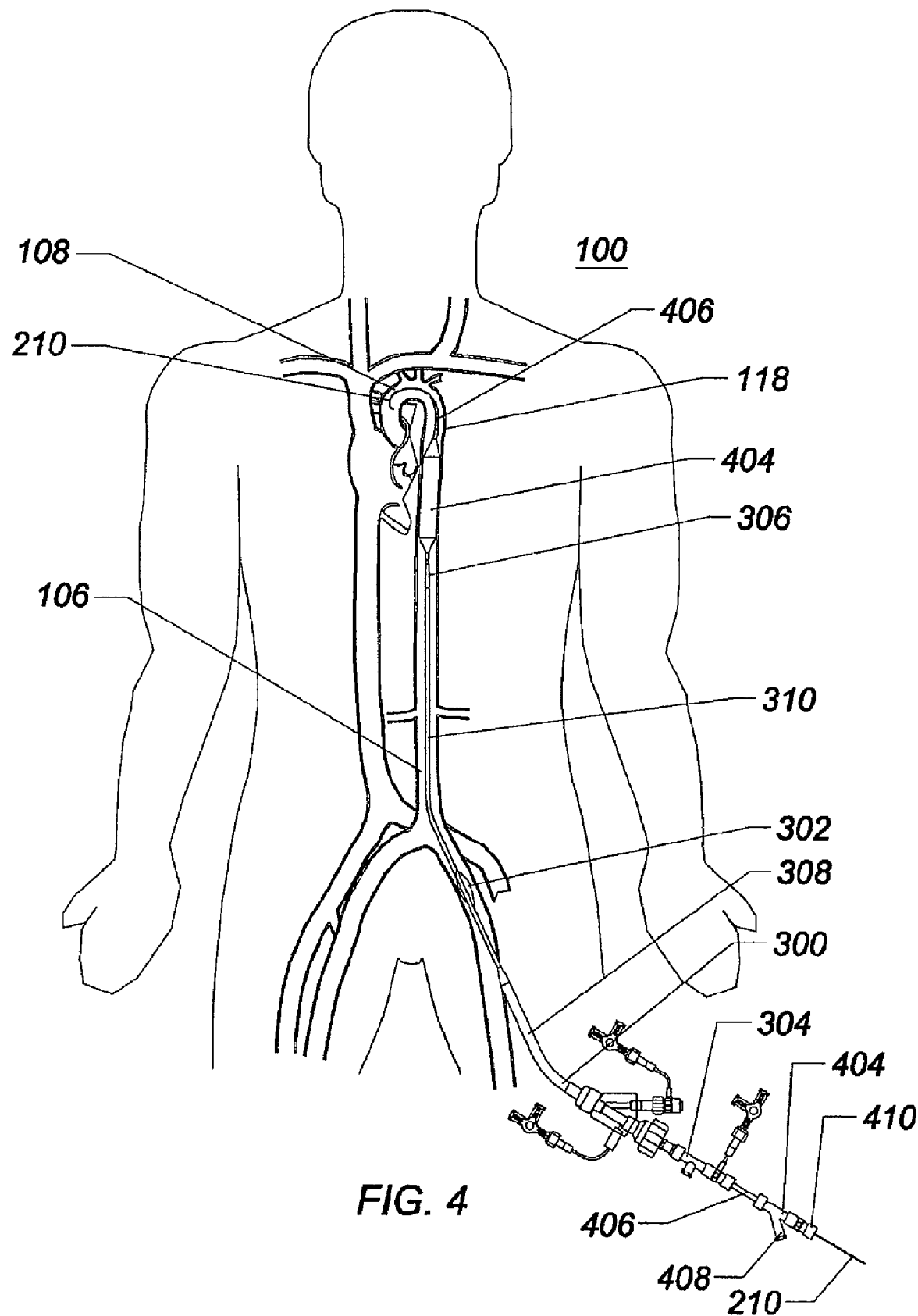
FIG. 4 is a cross-sectional illustration of the human central circulation with an IABP catheter located within the aorta, having been positioned through an expandable sheath, according to an embodiment of the invention.

FIG. 4 is a frontal illustration, looking posteriorly from the anterior side, of the patient 100. The expandable sheath 300 is inserted into the patient and routed to the thoracic aorta 118. The expandable sheath 300 comprises the proximal region 308 and the distal expandable region 310. The dilator 304 is inserted within the sheath 300 and an intra-aortic balloon pump catheter 400 is routed through the central lumen of the dilator 304. The intra-aortic balloon pump (IABP) catheter comprises the hub 404, the IABP catheter tubing 406, and the IABP balloon 404. The dilator 304 comprises the tip fairing 306. The hub 404 of the IABP further comprises the inflation port 408 and the guidewire port 410, through which the proximal end of the guidewire 210 extends. The distal end of the guidewire 210 resides within the aortic arch 108.

Referring to FIG. 4, the expandable distal region 310 remains unexpanded and small in diameter all the way from the incision 302 to the distal end of the expandable region 310. The proximal non-expandable region 308 resides outside the body so as not to require an incision 302 any larger than absolutely necessary during operation of the IABP. The IABP balloon 404 is shown inflated but during operation, is inflated and deflated continuously, generally in synchrony with the heartbeat, to provide counterpulsation to the pressure waveform in the descending aorta 118. This counterpulsation provides additional pressure to force blood into the coronary arteries (not shown) to improve cardiac circulation. The counterpulsation also raises arterial pressure which, in conjunction with closure of the aortic valve, augments pumping of blood to the systemic circulation.

FIG. 5a is a side view illustration of an intra-aortic balloon pump system 500 comprising an intra-aortic balloon pump (IABP) catheter 530, pre-mounted to a radially expandable sheath 532, further comprising a pre-mounted dilator 528. The radially expandable sheath 532 is shown in its collapsed, unexpanded configuration. The radially expandable sheath 532 comprises an expandable distal region 506, a non-expandable proximal region 504, a transition zone 508, and a sheath hub 502. The dilator 528 comprises a hub 524 further comprising a balloon inflation port 520, a dilator tube (not shown) having a central lumen (not shown), a dilator balloon inflation lumen or annulus (not shown), a dilator balloon (not shown), and a distal nose cone or fairing 510. The intra-aortic balloon pump catheter 530 further comprises a pumping balloon 514, a length of catheter tubing 512 having at least one guidewire lumen 534 (not shown) extending therethrough, a balloon inflation lumen or annulus (not shown), and an IABP catheter hub 516 further comprising a pumping balloon inflation port 518. The pumping balloon 514 is shown in its uninflated furled configuration wherein the wings that form in the thin wall of the deflated balloon 514 are wrapped around the catheter tubing 512.

Referring to FIG. 5a, guidewire lumen 534 of the intra-aortic balloon pump catheter 530 is sized sufficiently to slidably receive and pass over a standard medical guidewire sized from about 0.032 inches to about 0.040 inches. The pumping balloon 514 is affixed to the catheter tubing 512 by a proximal bond (not shown) and a distal bond (not shown). The interior space between the pumping balloon 514 and the catheter tubing 512 is operably connected to the balloon inflation lumen or annulus (not shown) by scythes or openings (not shown). The balloon inflation lumen or annulus (not shown) is affixed to and operably connected to the balloon inflation port 518 which is integral to, or affixed to the hub 516. The IABP catheter tubing 512 is sized to be received within the central through lumen (not shown) of the dilator 528. The IABP catheter tubing 512 can either be slidably received within the dilator tubing 536 (Refer to FIG. 5c) central through lumen or the IABP catheter tubing 512 can be slidably affixed within or integral to the central through lumen (not shown) of the dilator tubing 536. In an embodiment, the deflated pumping balloon 514, when furled tightly around its IABP catheter tubing 512, is capable of being slidably received within the central through lumen (not shown) of the dilator tubing 536. The dilator hub 524 is affixed to the proximal end of the dilator tubing 536 and the dilator inflation port 520 is affixed to the dilator hub 524. The lumen of the dilator inflation port 520 is operably connected to a lumen (not shown) within the dilator hub 524 which is, in turn, operably connected to the dilator inflation lumen or annulus (not shown). The distal fairing or nose cone 510 is affixed to the dilator tubing 536 distal to the dilator balloon (not shown). The dilator balloon (not shown) is affixed near the distal end of the dilator tubing 536 by a plurality of bonds. The sheath hub 502 is affixed to the proximal end of the proximal non-expandable region 504 of the sheath tubing. The distal end of the proximal non-expandable region 504 is affixed to the proximal end of the transition zone 508, while the distal end of the transition zone 508 is affixed to the proximal end of the expandable region 506 of the sheath tubing.

In an embodiment, the IABP catheter 530 moves axially in concert with the dilator 528, although 1 to 1 motion is not required and axial relative motion between the IABP catheter 530 and the dilator 528 can be beneficial for making position adjustments of the IABP catheter 530 when the sheath 532 and dilator 528 are located appropriately. The entire system 500 is typically advanced over an already placed guidewire to a target location in the vasculature, for example in the thoracic aorta, in the configuration shown in FIG. 5a. The dilator balloon (not shown) is preferably an angioplasty-type, non-elastomeric balloon and is fabricated from materials such as, but not limited to, polyester, polyamide, cross-linked polyolefin, or the like. The proximal region 504, the transition zone 508, and the distal region 506 of the sheath 532 can be fabricated from materials such as, but not limited to, polyethylene, high and low density polyethylene blends, polyester, Hytrel, polyurethane, polyvinyl chloride, polypropylene, polytetrafluoroethylene, and the like. Reinforcing materials such as, but not limited to, coils, braids, or scaffolds of PET, PEN, stainless steel, tantalum, gold, platinum, titanium, or other malleable biocompatible metal can be used to enhance the properties of the proximal region 504, the transition zone 508, and the distal region 506. The lumen within the dilator shaft is operably connected to the interior of the balloon by way of scythes or other openings. The nose cone or tapered fairing tip 510 is affixed near the distal end of the dilator tubing 536 and is fabricated from thermoplastic elastomer such as, C-Flex or from elastic polymers such as polyester, Hytrel, silicone elastomer, polyurethane, or the like. The tapered tip 510 can have a general funnel shape tapering from small at the distal end to large at the proximal end. In another embodiment, the tapered dilator tip 510 can have a complex taper with two or more angles and can also include intermediate cylindrical, non-tapered, regions. The tapered tip 510 can be made to expand with the distal end of the dilator balloon (not shown) and then shrink down with the dilator balloon (not shown) when it is deflated, facilitating withdraw through the lumen of the expanded distal region 506 of the sheath 532. The tapered fairing 510 can be asymmetric to substantially match the cross-sectional configuration of an expandable sheath section 506 that is folded and has inherently axial asymmetry.

FIG. 5b illustrates a side view of the intra-aortic balloon pump system 500 of FIG. 5a, wherein the distal expandable region 506 has been expanded by the dilator balloon (not shown). The dilator balloon (not shown) has subsequently been deflated and collapsed. The pumping balloon 514 on the IABP catheter 530 is shown in its inflated state. Expansion of the dilator balloon (not shown) is performed by injection of liquid such as, but not limited to, saline or radiopaque solutions into the dilator balloon inflation port 520 under pressure as generated by a commercial inflation device. Typical inflation pressures suitable for such inflation range from about 1 to about 30 atmospheres and preferably from about 5 to about 20 atmospheres. Pulsatile expansion and deflation of the pumping balloon 514 is typically accomplished using gas such as carbon dioxide or helium, both of which can dissolve within the cardiovascular system, should a leak occur, rather than causing an embolus that could lead to tissue ischemia. Inflation and deflation typically occurs over a cycle consistent with that of the human heart cycle, ranging, for example between about 40 and about 200 beats per minute. Maximum inflation pressure for the pumping balloon 514 is generally in the range of about 50 to about 300 mm Hg and preferably between about 80 and about 200 mm Hg. Gas is preferred for inflation of the pumping balloon 514 because of the small diameter of the inflation lumen or annulus (not shown) within the tubing 512 of the IABP catheter 530 and its inability to pass liquids in sufficient volumes over a heart cycle to adequately cause counterpulsation. The intra-aortic balloon catheter 530 further comprises a pressure measurement port 538 affixed to the IABP catheter hub 516, which is operably connected to a lumen (not shown) within the IABP catheter tubing 512, said lumen (not shown) extending to a point near the distal end of the IABP catheter 530 wherein the lumen (not shown) is exposed to the ambient environment. The IABP catheter hub 516 further comprises a pressure measurement port 538, affixed to the hub 516 and operably connected to a pressure measurement lumen within the IABP catheter tubing 512.

Referring to FIG. 5b, the IABP catheter tubing 512 and the pumping balloon 514 can be fabricated from materials such as, but not limited to, polyethylene, polypropylene, polyester, Hytrel, polyurethane, and the like. The IABP catheter hub 516 can be fabricated from similar materials as those used for the catheter tubing 512 and the pumping balloon 514 but the hub 516 can also be fabricated from polyvinyl chloride (PVC), acrylonitrile butadiene styrene (ABS), and the like. The pumping balloon 514 can be heat or ultrasonically welded to the IABP catheter tubing 512. The tapered fairing 510 has collapsed to a diameter small enough to fit within the lumen of the expandable region 506 since the dilator balloon (not shown) has been deflated. The configuration shown in FIG. 5b is suitable for the time just prior to removal of the IABP catheter 530 from the patient. The distal expandable region 506 is now enlarged so the skin incision and arterial penetration site is now enlarged such that a minimum of time in this configuration is beneficial.

FIG. 5c illustrates a side view of an intra-aortic balloon catheter and sheath system 500 wherein the sheath dilator 528 and intra-aortic balloon pump catheter 530 are being withdrawn proximally relative to the expandable sheath 532. The pumping balloon 514 has been deflated but retains its bag like perimeter which folds into a plurality of pleats, called wings, following fluid removal. In the illustrated embodiment, the wings are oriented perpendicular to the direction of view. These wings can cause damage to the lining of the vasculature as the deflated pumping balloon is being withdrawn from the patient. By withdrawing the pumping balloon 514 into the expanded sheath 506, the lining of the vasculature is protected from the wings. Both the dilator 528 and the intra-aortic balloon pump catheter 530 are being withdrawn proximally substantially in alignment.

FIG. 6a illustrates a side view of an intra-aortic balloon catheter and sheath system 600 wherein the sheath dilator 628 comprises a lead-in introducer 602 affixed at or near the distal end of the dilator 628. The IABP catheter sheath system 600 comprises the expandable sheath 632, further comprising the sheath hub 502, the proximal non-expandable region 504, the transition region 508 and the distal expandable region 506. The IABP catheter sheath system 600 comprises the dilator 628, which further comprising the dilator hub 524, a balloon inflation port 520, a dilator balloon (not shown), the dilator tubing (not shown), the lead in introducer 602, a sterile barrier 640, a proximal sterile barrier seal 644, a distal sterile barrier seal 642, and the tapered distal fairing 510. The IABP catheter sheath system 600 comprises the IABP catheter 530, further comprising the IABP balloon 514, the IABP catheter tubing 512, the IABP hub 516, the IABP balloon inflation port 518, and the guidewire port 526.

Referring to FIG. 6a, the length of the lead in introducer 602 can range from about 1 inch to about 36 inches, preferably from about 3 inches to about 10 inches, and more preferably from about 5 inches to about 8 inches. The diameter of the lead in introducer 602 can range between about 5 French and about 12 French, preferably between about 6 French and about 10 French and more preferably between about 7 French and about 9 French. The lead in introducer 602 is affixed, at its proximal end, to the distal end of the dilator central tubing 536 and the through, or guidewire, lumen of the dilator central tubing 536 is operably connected to the central lumen of the lead in introducer 602. The inner lumen diameter of the lead in introducer 602 and the sheath dilator 628 can range from about 3 French to about 10 French and preferably between about 4 French and about 8 French. The lead in introducer 602 can be permanently affixed to the distal end of the dilator central tubing 536 or it can be removably affixed thereto. The lead in introducer 602 can comprise a weakened area disposed longitudinally or spirally along its length to provide for tear away, or splitting characteristics, thus facilitating removal of the lead in introducer 602 should that be desired prior to advancing the expandable portion 506 of the sheath 632 and the tapered nose cone 510 into the percutaneous or surgical access site to the patient's vasculature. It is advantageous for the lead in introducer 602 to be small in diameter since it resides within the femoral or iliac artery during the pumping period which can last up to a week or more and a smaller diameter lead in sheath will have less chance of blocking blood flow to the distal femoral arteries, the legs, etc.

Referring to FIG. 6a, the IABP catheter sheath system 600 is introduced into the patient by first advancing a guidewire through a percutaneous incision or stick into the patient's iliac artery, femoral artery, or other suitable arterial access site through a hollow needle, typically around 18-gauge in size. The IABP catheter sheath system 600 is advanced distally over the guidewire into the incision until the lead in introducer 602 has passed through the skin and its distal end resides within the arterial access site. The IABP catheter 530 can now be introduced, with its pumping balloon 514 furled about the catheter shaft 512, into the sheath dilator 528, through the lead in introducer 602, and out the distal end of the lead in introducer 602 following which time it is routed to the treatment site, which is generally 2-5 cm downstream of the aortic arch within the thoracic aorta. In order to minimize the required working length of the IABP catheter 530, the proximal, non-expandable region 504 is reduced as much as possible or eliminated. In an embodiment, the sheath hub 502 can be directly affixed to the transition zone 508. The length of the expandable region 506 can range between about 2 inches and about 24 inches and preferably between about 6 and about 18 inches such that, when introduced into the vasculature, it is capable of lining the entire femoral, iliac and descending aortic tract between approximately the renal arteries to the aortic bifurcation and the vascular access site.

The sterile barrier 640 surrounds the outside diameter of the sheath 632 and is affixed at its proximal end to the proximal sterile seal 644. The sterile barrier 640 is affixed at its distal end to the distal sterile seal 642. The sterile barrier 640 can be configured to telescope, accordion, or otherwise accommodate axial or longitudinal shortening. The sterile barrier 640 and the proximal and distal seals 644 and 642 comprise structures that prevent migration of microbes across their boundaries. The proximal seal 644 can be affixed to the proximal portion 504 of the sheath 632 or it can be affixed to the sheath hub 502. In another embodiment, the proximal seal 644 can be slidably movable along the longitudinal axis of the proximal portion 504 but always maintains a complete, or nearly complete, sterile barrier by means of a seal. The seal can be achieved using a soft elastomeric gasket, O-ring, or the like. The slidability can be enhanced by means of lubricious materials in the proximal seal 644 or the proximal portion 504 such as, but not limited to, PTFE, FEP, polyethylene, hydrogel, polypropylene, silicone lubricants, or the like. The distal seal 642 can be slidably movable along the longitudinal axis of the distal portion 506 of the sheath 632. The distal seal 642 is configured to maintain a complete, or nearly complete, sterile seal against the distal portion 506. The distal seal 642 can be configured similarly to the proximal seal 644 using similar materials. The distal seal 642, however, seals against an outer surface 506 which is not complete and unbroken, but which can comprise one or more longitudinal fold. Thus, the distal seal 642 can be comprised, on its internal aspect of gap-filling, swellable material such as open or closed cell foam, hydrogel, or very soft elastomer such as, but not limited to, thermoplastic elastomer or silicone elastomer with a durometer of 5 A to 30 A. The distal seal 642 can be thicker than the proximal seal 644 and can be pre-compressed to a greater extent than that of the proximal seal 644 to permit accommodation of uneven sheath exterior contours, as well as to accommodate for radial expansion of the distal region 506 in the range of about 1.2× to about 5× its original radius. The length of the sterile barrier 640 can range from about 1-cm to about 90-cm and preferably range from about 10-cm to about 50-cm.

FIG. 6b illustrates the IABP catheter sheath system 600 wherein the IABP balloon 514 has been inflated and the sheath subsystem 632 has been advanced distally relative to the IABP catheter 530. Note the distance between the distal end of the lead in sheath 602 and the IABP balloon 514 and the amount of exposed IABP catheter tubing 512 has been significantly reduced relative to that shown in FIG. 6A. The sterile barrier 640 is collapsed linearly, or axially, with the proximal seal 644 substantially unchanged in its position. The distal seal 642 has remained affixed to the sterile barrier 640 but has moved proximally along the distal region 506 so that the distal region 506 can be advanced into a patient. The distal expandable region 506 is radially, or diametrically, collapsed and, as yet, unexpanded. The transition zone 508 affixed to and between the distal expandable region 506 and the proximal non-expandable region 504 is still visible. The amount of IABP catheter tubing 512 exposed proximally between the dilator hub 524 and the IABP catheter hub 516 is increased relative to that shown in FIG. 6a. The dilator hub 524 comprises the dilator balloon expansion port 520, which is affixed thereto and which is further operably connected to the interior of the dilator balloon (not shown) by an inflation lumen or annulus (not shown) within the dilator tubing.

FIG. 6c illustrates the IABP catheter sheath system 600 wherein the IABP balloon has been deflated to form what is now a flat bag. The distal expandable region 506 has been expanded using the dilator balloon (not shown) having been inflated through the dilator balloon inflation port 520. The distal nose cone or fairing 510 on the dilator is expanded around the distal end of the dilator balloon (not shown). The dilator 618 passes through the Tuohy-Borst or other hemostasis valve 522 at the proximal end of the hub 502 of the sheath subsystem 632. The dilator balloon (not shown) is preferably an angioplasty-type unfurling balloon with bonds at its proximal and distal end. The balloon (not shown) is fabricated from high-strength materials such as, but not limited to, PET, polyamide, cross-linked polymers, polyethylene, and the like. The dilator balloon (not shown) and dilator 628 can be fabricated to generate pressures of up to about 20 to about 30 atmospheres without leakage or failure. The dilatation balloon (not shown) is in its expanded, inflated configuration over the inner dilator tubing (not shown). When the dilator balloon (not shown) is deflated in a subsequent step, the distal shroud 510 collapses diametrically and be pulled or withdrawn proximally through the expanded tubing 506 as the dilator 628 is being withdrawn. The sterile barrier 640 is unchanged in length and the position of the proximal seal 644 and the distal seal 642 remain substantially unchanged from FIG. 6b. However, the inner diameter of the distal seal 642 has increased to accommodate the expanding distal region 506 of the sheath 632. In another embodiment, the distal seal 642 can be made removable to permit expansion of the distal region 506.

Figure 7:
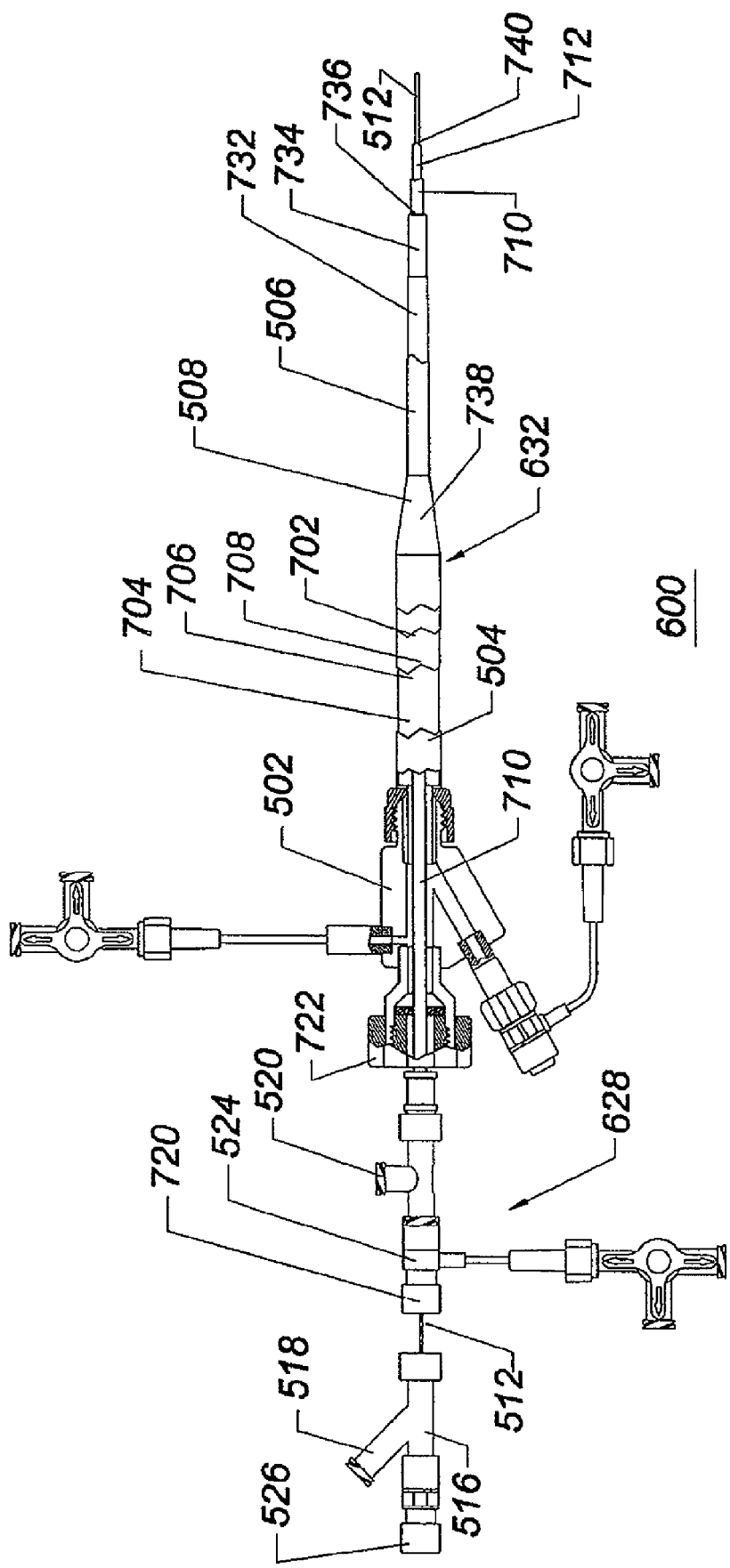
FIG. 7 is a side view illustration of the proximal end of the IABP sheath system with the sheath hub and sheath tubing shown in partial breakaway view, according to an embodiment of the invention.

FIG. 7 illustrates a breakaway view of the proximal end of an embodiment of the IABP sheath dilator system 600. The proximal region 504 of the sheath 632 comprises an outer layer 702, an inner layer 704, and a reinforcing layer 706. The proximal region can also comprise an optional elastomeric layer 708. The dilator 628 comprises the dilator hub 524 further comprising the balloon inflation port 520, a dilator outer tubing 710, and a length of dilator inner tubing 712 having a dilator central lumen 740. The IABP catheter 630 comprises the IABP hub 516, the IABP catheter tubing 512, the pumping balloon inflation port 518, and the guidewire port 526. The sheath 632 further comprises the transition zone 508, the distal sheath tubing 506 further comprising a distal sheath outer layer 738, a distal sheath inner layer 734, and a distal sheath intermediate reinforcing layer 732. The interior of the sheath inner layer 734 comprises a sheath through lumen 736.

Referring to FIG. 7, the proximal sheath tubing 504, the distal sheath tubing 506, or both, as well as the transition zone 508, can be fabricated using composite construction comprising the inner layer 704, a reinforcing layer 706, and an outer layer 702. Suitable materials for use in fabricating the inner layer 704 and the outer layer 702 include, but are not limited to, polyurethane, polyethylene, polypropylene, Hytrel, PEBAX, polyamide, blends of high-density and low-density polyethylene, C-Flex, and the like. Wall thicknesses of these layers 702 and 704 can range from about 0.0005 to about 0.025 inches and preferably between about 0.001 and about 0.010 inches. In another embodiment, an elastomeric layer 708 can be disposed outside the reinforcing layer 706 and under the outer layer 702. In yet another embodiment, an elastomeric layer 708 can be disposed between the reinforcing layer 706 and the inner layer 704. The elastomeric layer 708 can be fabricated from materials such as, but not limited to, thermoplastic elastomer, silicone elastomer, polyurethane elastomer, C-Flex, or the like. The cross-sectional shape of the proximal tubing 504 can further be configured as non-circular to minimize the cross-sectional area while two round catheters, such as diagnostic catheters, are inserted therethrough. The proximal reinforcing layer 706 can be fabricated from materials such as, but not limited to, stainless steel, tantalum, titanium, nitinol, cobalt-nickel alloys, or the like. The coil or braid in the proximal reinforcing layer 706 can also be fabricated from polymers such as PET, PEN, polyamide, HDPE, or the like. In an exemplary embodiment, the reinforcing layer 706 is a braid of PEN.

Referring to FIG. 7, the distal section of the sheath 632 further comprises the outer dilator tubing 710, the inner dilator tubing 712, and a central dilator through lumen 740. The distal sheath tubing 506 can be a composite structure fabricated from an inner layer 734, the intermediate reinforcing layer 732, and the outer layer 738. In an embodiment, the intermediate reinforcing layer 732 can be fabricated from a coil, braid, or stent-like shape of wire, mesh, polymer, or other material. The reinforcing layer 732 in the distal region 506 can advantageously possesses malleable characteristics and can be fabricated from stainless steel, tantalum, titanium, nitinol, cobalt-nickel alloys, or the like. In an exemplary embodiment, the malleable reinforcement layer 732 comprises a coil of stainless steel 304, which has been substantially annealed. The stainless steel can be formed into a flat wire with a thickness of about 0.002 to about 0.005 inches and a width of about 0.010 to about 0.040 inches. The flat wire is formed into a coil with a spacing substantially the same as the width of the flat wire. The stainless steel wire can be coated with a layer of radiopaque material such as gold, tantalum, platinum, or the like, to a thickness of about 100 angstroms or more to enhance its radiopacity. The coil configuration of the reinforcing layer 732 can be fabricated from flat wire or from round wire. The sheath hub 502 can comprise a hemostasis valve 722. In the illustrated embodiment, the hemostasis valve 722 on the sheath hub 502 is a large bore valve which can be, for example, a Tuohy-Borst valve, duckbill valve, annulus seal, or other valve. The dilator hub 524 can comprise a hemostasis valve 720 that can be a Tuohy-Borst valve, duckbill valve, annulus seal, or other valve. The IABP catheter tubing 512 can be slidably movable, in the axial direction, within the inner lumen 740 of the dilator inner tubing 712.

FIG. 8a is a side view of the distal region of the sheath system 600 comprising the sheath 632 and the dilator 628, in its diametrically collapsed configuration. The sheath 632 further comprises the distal expandable tubing 506, the transition zone 508, a sheath RO marker 816, and one or more longitudinal folds 802. The dilator 628 comprises the dilator inner tubing 712 further comprising a through lumen 740, a radiopaque marker 804, a dilator balloon 510 further comprising a dilator balloon bond 814, and a distal fairing 810 further comprising a fairing bond 812. The IABP catheter tubing 512 is also illustrated.

Referring to FIG. 8a, the radiopaque markers 804 on the dilator 628 can all be configured as the non-expandable type and can be affixed to the dilator inner tubing 712 using adhesive, compression fit, interference fit, potting, overmolding, encapsulation, welding, or the like. The radiopaque markers on the dilator 628 can be fabricated as short, axially elongate hollow cylinders using materials such as, but not limited to, platinum, gold, tantalum, iridium, barium, bismuth, or the like. The illustrated distal tip radiopaque marker 804 can be affixed over the distal dilator balloon bond 814 for ease of assembly and is generally covered by the distal shroud or fairing 810. The radiopaque markers on the dilator can be affixed to the inner tubing 712 prior to attachment of the dilator balloon 510. The inclusion of the radiopaque markers facilitates fluoroscopic visualization of the expandable portion of the sheath system 600. A distal marker on the dilator 628 can facilitate fluoroscopic visualization of the distal tip of the dilator 628 to ensure that the dilator 628 does not impinge on, perforate, or damage vascular or other tissue structures within the body and that the dilator 628 follows the desired path within the patient. The sheath 632 can also comprise radiopaque markers 816. These radiopaque markers 816 on the sheath 632 can be affixed to, or embedded within, the expandable region 506. The radiopaque markers 816 on the sheath 632 can be made to be expandable and can be configured as coils of folded radiopaque wire embedded within the folded walls of the sheath 632. The longitudinal fold 802 terminates at or near the proximal end of the transition zone 508. The longitudinal fold 802 is used to furl excess sheath wall out of the way when the sheath expandable region 506 is in its collapsed configuration. The number of folds 802 can vary between 1 and 10 with a preferred range of 2 to 5. The IABP catheter 512 can be advanced ahead of the dilator 628 so it never has to be withdrawn inside the inner lumen 740 of the dilator inner tubing 712 but can be removed through the sheath 632 when the dilator 628 is removed from the sheath 632. The distal fairing 810 is elastomeric and its proximal end can cover the distal end of the sheath tubing 506. The distal fairing 810 can serve to protect the balloon 510 and the distal balloon to dilator tubing bond 814.

FIG. 8b illustrates the distal end of the sheath system 600 wherein the expandable tubing 506 has been expanded diametrically by the dilator balloon 510 which has been expanded under the pressure of fluid being injected between the dilator balloon 510 and the dilator inner tubing 712. Typical fluid pressures suitable for such sheath expansion range from about 3 to about 50 atmospheres and preferably between about 5 and about 30 atmospheres. The sheath radiopaque marker 816 has unfolded with the sheath distal tubing 506 so that the fold line 802 from FIG. 8a is no longer visible. The proximal end of the fairing tip 810 has expanded diametrically by the balloon 510 and can be withdrawn distally to expose the distal edge 818 of the sheath tubing 506. At this point, the balloon 510 can be deflated and the fairing tip 810 will elastically recoil to a diameter small enough to pass through the inner lumen of the sheath tubing 506 for proximal withdrawal. Once the balloon 510 has been inflated and deflated, the IABP catheter tubing 512 and any associated IABP balloons (not shown) can also be withdrawn proximally.

FIG. 9a illustrates a sheath system 910 comprising a sheath dilator 900 further comprising an integral intra-aortic balloon pump balloon 514. The sheath 910 comprises the expandable distal region 506, the transition zone 508, the proximal non-expandable region 504, and the sheath hub 502. The dilator 900 further comprises the pumping balloon 514, the dilator tubing assembly 906, the dilator balloon 510, a radiopaque marker 914, and the dilator hub 902 further comprising the purge port 904, the sheath dilator inflation port 520, the pumping balloon inflation port 518, and the guidewire port 526.

Referring to FIG. 9a, the pumping balloon 514 is affixed to the dilator tubing assembly 906 proximate its distal end by bonds at each end of the balloon 514. The pumping balloon 514 is inflated and deflated through a lumen (not shown) within the dilator tubing assembly 906 which is operably connected with the space inside the pumping balloon 514 and the pumping balloon inflation lumen 518. The dilator balloon 510 is affixed to the dilator tubing assembly 906 by bonds at each end of the balloon 510. The dilator balloon 510 is operably connected to the dilator inflation port 902 by a separate lumen (not shown) running substantially the length of the dilator tubing assembly 906. A central lumen within the dilator tubing assembly 906 is operably connected to the guidewire port 526. The guidewire port 526 can be terminated at or near its proximal end with a hemostasis valve, Tuohy-Borst valve, or the like.

FIG. 9b illustrates the intra-aortic balloon pump and sheath of FIG. 9a wherein the pumping balloon 514 is inflated to its maximum volume. The expandable region of the sheath 506 and the dilator balloon 510 remain unexpanded. This is the configuration in which the system would be maintained during the counterpulsation of the pumping balloon 514.

FIG. 9c illustrates the intra-aortic balloon pump and sheath of FIG. 9a wherein the dilator balloon 510 is inflated under pressures of, for example about 5 to about 40 atmospheres and preferably from about 10 to about 30 atmospheres. When it becomes time to deflate the pumping balloon 514 and remove it from the body, the dilator balloon 510 can be inflated, as illustrated, under pressure to expand the expandable region of the sheath. At this point, the dilator balloon 510 is deflated and withdrawn into the expanded sheath 910 or it is completely removed from the expanded sheath 901, with the pumping balloon 514 and its associated dilator tubing 906 removed therewith or withdrawn inside the sheath expandable distal region 906.

Aspects of the invention include the methods of use of the IABP sheath in conjunction with an IABP catheter and pumping system. The IABP catheter is used in conjunction with an IABP pumping system. The balloon inflation port near the proximal end of the IABP catheter is operably connected to the outlet of the IABP pumping system, generally by way of a connector line. The IABP pumping system is a pulsatile device that generates and then relieves pressure at its outlet at a rate that is set on the console or is driven from a trigger circuit operably connected to an electrocardiogram (ECG) measuring device which acquires electrocardiogram data from the patient. The IABP pumping system is generally a piece of hardware that is situated on a roll-around cart or on a stand near the patient. The gas generally used for pumping the IABP pumping balloon is helium, although carbon dioxide or other gasses may be considered suitable. The choice of gas is generally made based on the ability of the gas to dissipate if it leaks into the cardiovascular system, although the viscosity of the gas is important in designing the smallest possible diameter IABP catheter.

FIG. 10a illustrates a side view of the IABP sheath catheter system 910 wherein the dilator balloon (not shown) has been deflated, as has the IABP balloon 514. The IABP sheath catheter system 910 comprises the IABP balloon catheter dilator 900, further comprising the IABP balloon 514 affixed to the IABP catheter dilator tubing 906, one or more radiopaque markers 914, the IABP catheter dilator hub 902, the purge port 904, the dilator inflation port 520, the IABP balloon inflation port 518, the guidewire port 526, and the dilator balloon (not shown). The IABP sheath catheter system 910 also comprises the expandable sheath 920 further comprising the expandable distal region 506, the transition zone 508, the proximal region 504, and the sheath hub 502. The IABP balloon catheter dilator 900 is being withdrawn proximally within the sheath and the IABP balloon 514 is being re-folded and collapsed within the distal region 506.

FIG. 10b illustrates an enlarged view of the distal end of the IABP sheath catheter system 910 following deflation and collapse of the IABP balloon 514. The width of the IABP balloon 514 is greater following re-collapse, than in its inflated state, since the IABP balloon 514 has collapsed and its full circumference is folded into a nearly 2-dimensional shape, called a wing 1002. It is this wing 1002, or plurality of wings 1002, that can cause damage to the vasculature during removal of the deflated IABP balloon 514 and from which re-sheathing within the sheath 506 will protect or shield the arterial wall. The force to withdraw the IABP balloon 514 is transferred through the IABP dilator catheter shaft 906, to which the IABP balloon 514 and the dilator balloon (not shown) are both affixed. In this view, the catheter shaft 906 is visible under the IABP balloon 514 since the IABP balloon 514 is a generally transparent structure fabricated from relatively clear polymers.

FIG. 10c illustrates a front view of the distal end of the IABP sheath catheter system 910 following deflation and collapse of the IABP balloon 514, further illustrating the wing-shaped IABP balloon 514 following deflation. In this embodiment, the IABP balloon 514 has formed two wings 1002. The catheter shaft 906 is visible as well as the leading edge of the expandable distal region 506 of the sheath. Referring to FIGS. 10a and 10c, the wings 1002 can form very sharp, stiff structures, held in place by the vacuum generated by a vacuum generating device (not shown) which is operably connected to the IABP balloon 514 for deflation by way of port 518.

The present invention may be embodied in other specific forms without departing from its spirit or essential characteristics. For example, the sheath may include instruments affixed integrally to the interior central lumen of the sheath, rather than being separately inserted, for performing therapeutic or diagnostic functions. The sheath hub may comprise tie downs or configuration changes to permit attaching the hub to the mouth, nose, or face of the patient. The dilatation means may be a balloon dilator as described in detail herein, or it may be a translation dilator wherein an inner tube is advanced longitudinally to expand an elastomeric small diameter tube. The sheath or introducer described herein can be used for other large therapeutic catheters including those, for example, intended to perform balloon valvuloplasty. Various valve configurations and radiopaque marker configurations are appropriate for use in this device. The IABP catheter can be longitudinally affixed to the dilator or it can be slidably constrained relative to the dilator. The described embodiments are to be considered in all respects only as illustrative and not restrictive. The scope of the invention is therefore indicated by the appended claims rather than the foregoing description. All changes that come within the meaning and range of equivalency of the claims are to be embraced within their scope.

What is claimed is:

1. A method of instrumenting the aorta of a patient for the purpose of introducing and removing an intra-aortic balloon pump catheter comprising the steps of:
   routing a guidewire into the aorta from a femoral or iliac artery access point on a patient;
   inserting a sheath with a pre-inserted dilator into the patient's femoral or iliac artery over the guidewire, and advancing the sheath to a treatment or diagnostic site within the aorta, wherein the sheath comprises a distal expandable region which is collapsed in diameter;
   introducing an intra-aortic balloon pump catheter into the aorta of the patient through the sheath;
   performing counterpulsation with the intra-aortic balloon pump catheter;
   expanding a dilator within the sheath, thus expanding the distal region of the sheath, wherein a frill-size lumen exists within at least the distal region of the sheath;
   collapsing the dilator by an action applied at the proximal end of said dilator;
   withdrawing the dilator from the distal, expandable region of the sheath;
   withdrawing the deflated intra-aortic balloon pump catheter into the distal, expandable region of the sheath; and
   removing the sheath and intra-aortic balloon pump catheter from the patient.

2. The method of claim 1 wherein the expanding a dilator step is performed by inflating a balloon on the dilator.

3. The method of claim 1 wherein the expanding a dilator step is performed by attaching a liquid-filled inflation device to a balloon inflation port at the distal end of the dilator and infusing liquid under pressure into the dilator.

4. The method of claim 1 wherein the step of collapsing the dilator comprises withdrawing a plunger on the inflation device to withdraw liquid from the dilator.

5. The method of claim 1 wherein the intra aortic balloon catheter is withdrawn completely through the sheath and removed from the proximal end of the sheath prior to the sheath being removed from the patient.

6. The method of claim 1 wherein the full-size lumen created in the expandable region of the sheath by the dilator is substantially larger than a lumen of a proximal non-expandable region of the sheath.

7. The method of claim 1 wherein the full-size lumen created in the expandable region by the dilator is substantially smaller than a lumen of the proximal region of the sheath.

8. The method of claim 1 wherein the full-size lumen created in the expandable region by the dilator is substantially the same size as a lumen of the proximal region of the sheath.

9. A method of introducing and removing an intra-aortic balloon pump catheter comprising:
   inserting at least a portion of an introducer into a patient's femoral or iliac artery, the introducer comprising a sheath, a pre-mounted dilator, and a intra-aortic balloon pump, the sheath comprising a collapsed distal region, the dilator comprising a dilator balloon positioned within the distal region of the sheath, the intra-aortic balloon pump comprising a pump balloon positioned distal to the dilator and the distal region of the sheath;
   advancing the pump balloon to a treatment or diagnostic site within the aorta;
   performing counterpulsation with the intra-aortic balloon pump catheter;
   advancing the collapsed distal region of the sheath to the treatment or diagnostic site;
   inflating the dilator balloon, thereby expanding the collapsed distal region of the sheath;
   deflating the dilator balloon;
   withdrawing the dilator balloon from the expanded distal region of the sheath;
   withdrawing the pump balloon into the expanded distal region of the sheath; and
   removing the sheath and pump balloon from the patient.

10. The method of claim 9, the dilator further comprising a central lumen and the intra-aortic balloon pump catheter further comprising a pump inflation lumen operably connected to the pump balloon and positioned at least partially within the central lumen of the dilator during counterpulsation, wherein counterpulsation is performed by inflating and deflating the pump balloon through the pump inflation lumen.

11. The method of claim 10, the dilator further comprising a dilator inflation lumen operably connected to the dilator balloon, wherein inflation and deflation of the dilator balloon is performed through the dilator inflation lumen.

12. The method of claim 11, the dilator further comprising a dilator hub positioned proximal to the sheath, and the intra-aortic balloon pump further comprising a pump hub positioned proximal to the dilator and the sheath, the dilator hub comprising a dilator inflation port operably connected to the dilator inflation lumen, the pump hub comprising a pump inflation port operably connected to the pump inflation lumen, wherein inflation of the dilator balloon comprises injecting fluid into the dilator balloon through the dilator inflation port and dilator inflation lumen, and inflation of the pump balloon comprises injecting fluid into the pump balloon through the pump inflation port and pump inflation lumen.

13. The method of claim 12, wherein at least one of the fluids injected into the dilator balloon and the pump balloon is a gas.

14. The method of claim 9, wherein at least the collapsed distal region of the sheath comprises an inner layer, an outer layer, and a malleable reinforcement between the inner layer and the outer layer.

15. The method of claim 14, wherein the malleable reinforcement comprises a metal coil.

16. The method of claim 9, wherein the collapsed distal region of the sheath comprises one or more longitudinal folds.

17. The method of claim 9, wherein the dilator further comprises a fairing positioned at a distal end of the dilator.

18. The method of claim 9, wherein the advancement of the pump balloon and the advancement of the collapsed distal region of the sheath are performed at the same time.

19. The method of claim 9, wherein the advancement of the collapsed distal region of the sheath is performed after the counterpulsation.

20. The method of claim 9, the introducer further comprising a lead-in introducer, the lead-in introducer positioned distal to the dilator balloon and comprising a central lumen, wherein inserting at least a portion of the introducer comprises:

inserting the lead-in introducer into the patient's femoral or iliac artery;

after insertion of the lead-in introducer, advancing the pump balloon distally through the central lumen of the lead-in introducer into the patient's femoral or iliac artery.

* * * * *

UNITED STATES PATENT AND TRADEMARK OFFICE
CERTIFICATE OF CORRECTION

| | |
|---|---|
| PATENT NO. | : 7,722,568 B2 |
| APPLICATION NO. | : 12/021097 |
| DATED | : May 25, 2010 |
| INVENTOR(S) | : Jay A. Lenker et al. |

It is certified that error appears in the above-identified patent and that said Letters Patent is hereby corrected as shown below:

In column 23, line 62, in Claim 1, change "frill-size" to --full size--.

Signed and Sealed this

Sixteenth Day of November, 2010

David J. Kappos
*Director of the United States Patent and Trademark Office*